United States Patent
Costanzo (12)

(10) Patent No.: US 6,323,219 B1
(45) Date of Patent: Nov. 27, 2001

(54) METHODS FOR TREATING IMMUNOMEDIATED INFLAMMATORY DISORDERS

(75) Inventor: Michael J. Costanzo, Ivyland, PA (US)

(73) Assignee: Ortho-McNeil Pharmaceutical, Inc., Raritan, NJ (US)

(*) Notice: Subject to any disclaimer, the term of this patent is extended or adjusted under 35 U.S.C. 154(b) by 0 days.

(21) Appl. No.: 09/238,882

(22) Filed: Jan. 27, 1999

Related U.S. Application Data

(63) Continuation-in-part of application No. 09/110,409, filed on Jul. 6, 1998
(60) Provisional application No. 60/080,441, filed on Apr. 2, 1998.

(51) Int. Cl.[7] .................. A61K 31/445; A61K 31/56; A61K 31/52
(52) U.S. Cl. ............... 514/317; 514/179; 514/263; 514/321; 514/826
(58) Field of Search ................... 514/317, 321, 514/179, 263

(56) References Cited

U.S. PATENT DOCUMENTS 5,523,308    6/1996    Costanzo et al. ............ 514/317

FOREIGN PATENT DOCUMENTS

| 8-20597 | 1/1996 | (JP) . |
|---|---|---|
| WO 96/19483 | 6/1996 | (WO) . |
| WO 96/19491 | 6/1996 | (WO) . |
| WO 96/30035 | 10/1996 | (WO) . |
| WO 96/30396 | 10/1996 | (WO) . |
| WO 96/37497 | 11/1996 | (WO) . |
| WO 98/05333 | 2/1998 | (WO) . |
| WO 98/09987 | 3/1998 | (WO) . |

*Primary Examiner*—Kevin E. Weddington
(74) *Attorney, Agent, or Firm*—Mary Appollina

(57) ABSTRACT

This invention relates to methods ands compositions for bringing about changes in skin pigmentation and for treating inflammatory disorders. More particularly, this invention relates to compounds which affect melanogenesis and can be used as depigmenting agents or as agents for darkening skin utilizing the PAR-2 pathway and compounds for the, prevention and treatment of immunomediated inflammatory diseases, particularly those associated with the respiratory tract, such as asthma and allergic rhinitis.

21 Claims, 25 Drawing Sheets

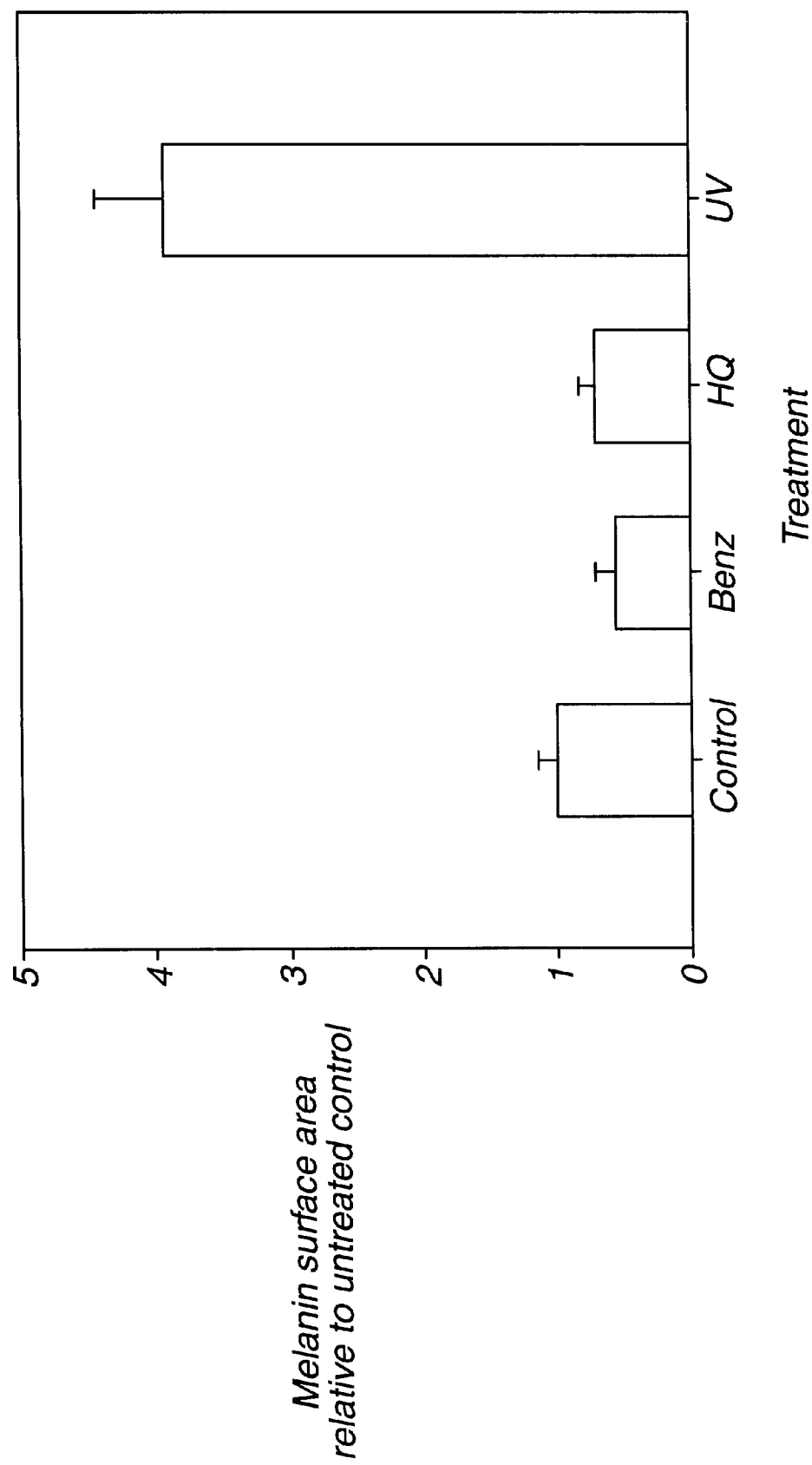

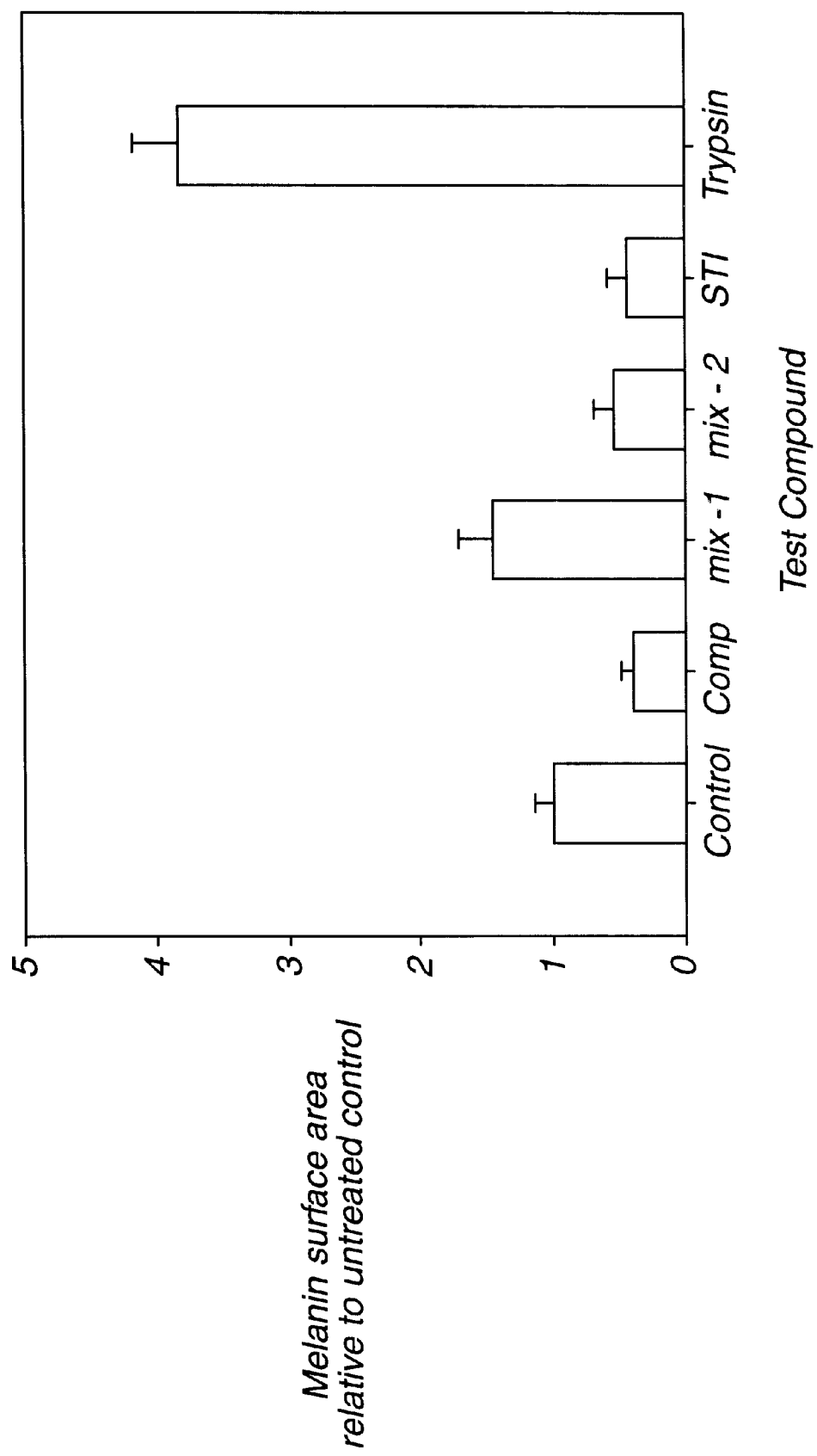

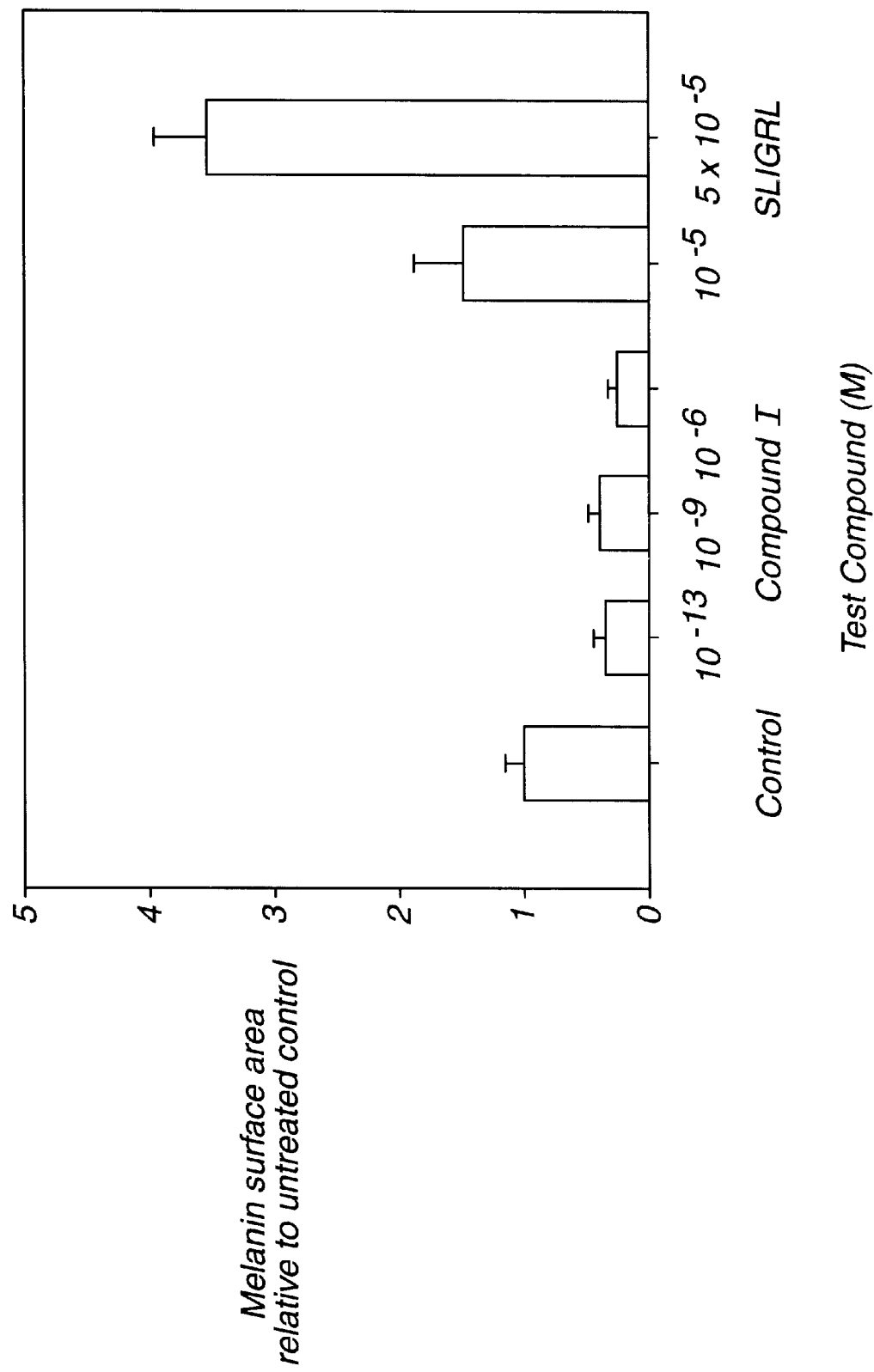

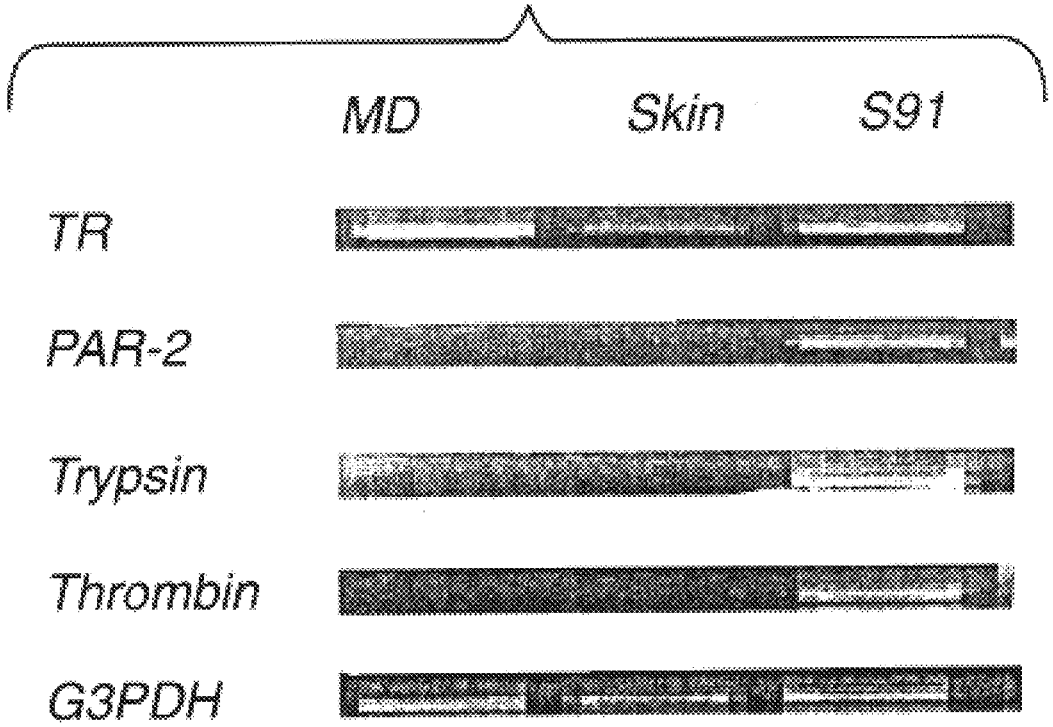

FIG. 5B
TR 
PAR-2 
Trypsin 
Thrombin 
G3PDH 

FIG. 6B
| SLIGRL μM | 0 | 2 | 10 | 50 |
|---|---|---|---|---|
| Tyrosinase |  | | | |
| TRP-1 |  | | | |
| TRP-2 |  | | | |
| Trypsin |  | | | |
| G3PDH |  | | | |

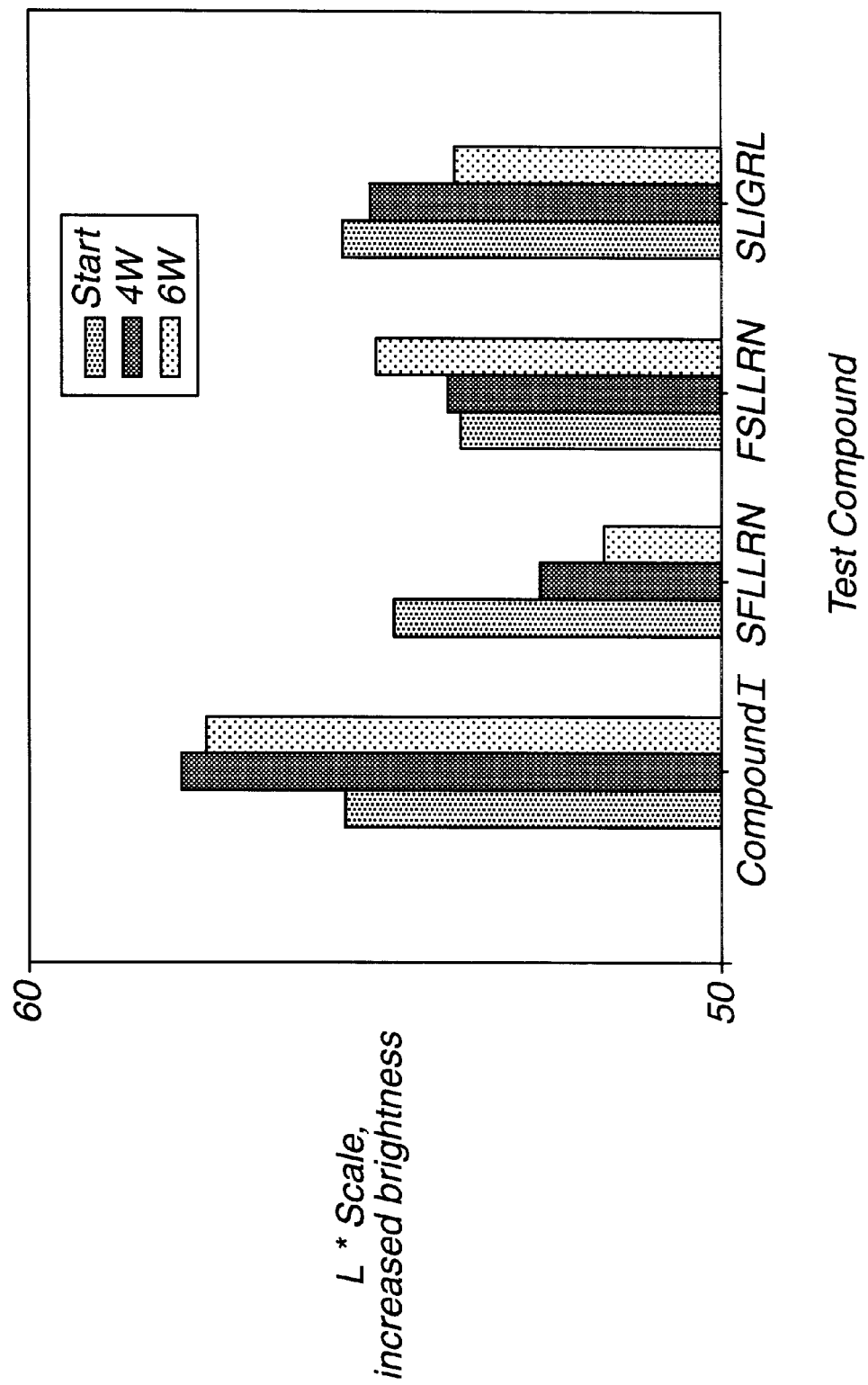

FIG. 11A
FIG. 11B
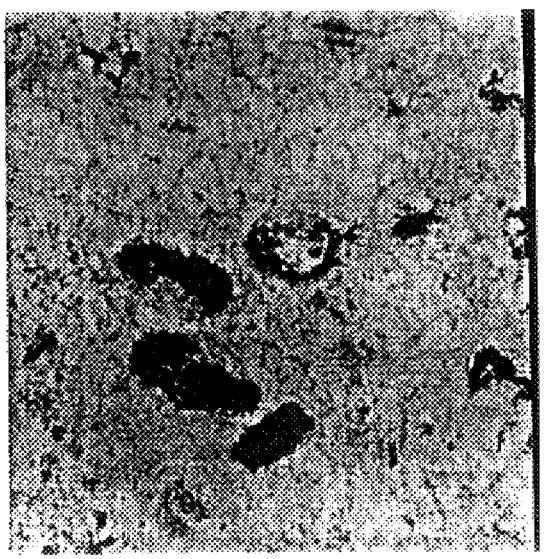

Untreated

+1 Week

+4 Weeks

METHODS FOR TREATING IMMUNOMEDIATED INFLAMMATORY DISORDERS

CROSS-REFERENCE TO RELATED APPLICATIONS

This application is a continuation-in-part applications Ser. No. 09/110,409, filed Jul. 6, 1998, which claims priority from provisional application Ser. No. 60/080,441, filed Apr. 2, 1998, the contents of all of which are hereby incorporated by reference.

FIELD OF THE INVENTION

This invention is related to methods and compositions for bringing about skin pigmentation and/or for causing skin depigmentation and/or methods for the prevention and treatment of immunomediated inflammatory disorders. More particularly, this invention relates to compounds which affect melanogenesis and can be used as depigmenting agents or as agents for darkening skin, and compounds for the prevention and/or treatment of immunomediated inflammatory diseases, especially those associated with the respiratory tract, such as asthma and allergic rhinitis.

BACKGROUND OF THE INVENTION

Skin coloring has been of concern to human beings for many years. In particular, the ability to remove hyperpigmentation, such as found in age spots, freckles or aging skin generally, is of interest to individuals desiring a uniform complexion. In certain areas of the world, general body whitening is desirable. There are also hypopigmentation and hyperpigmentation disorders that are desirable to treat. Likewise, the ability to generate a tanned appearance without incurring photodamage due to solar radiation is important to many individuals. There have been many methods proposed to accomplish depigmentation, as well as to accomplish darkening of the skin. For example, kojic acid, hydroquinone, retinoids and other chemical compounds have been used for depigmentation. Dihydroxyacetone and like chemical compounds have been utilized for their ability to "tan" the skin without exposure to the sun.

Many of these previous solutions have not been found acceptable. There is often a distinct line of demarcation between the areas of skin to which such previous compositions have been applied. Therefore, precise application of all these compounds is necessary in order to achieve the desired result. Many of these compounds have been found to be quite irritating to the skin and therefore undesirable for use.

The understanding of the chemical and enzymatic basis of melanogenesis is heavily documented. Melanocytes migrate from the embryonal neural crest into the skin to produce secretory granules, melanosomes, which produce melanin. Melanogenesis occurs within the melanosome, and the melanin is later distributed to keratinocytes via the melanocyte dendrites. The key enzyme in melanogenesis is tyrosinase, which initiates a cascade of reactions which convert tyrosine to the biopolymer melanin. Two tyrosinase-related proteins (TRP's) are known, TRP-1 and TRP-2. These proteins share with tyrosinase about 40% homology and have catalytic activities as well as regulatory roles in melanogenesis. TRP-1 is the most abundant glycoprotein in melanocytes.

In spite of the fact that the chemical and enzymatic basis of melanogenesis is well-documented, its regulation at the cellular level is only partially understood. Tyrosinase and the TRP's share structural and biological properties with the lysosomal-associated membrane protein (LAMP) gene family, therefore their targeting to the melanosomal membrane might induce their activation. A phosphorylation/dephosphorylation reaction at the cytoplasmic tails of these proteins could be involved in the regulation of melanogenesis. The beta isoform of the Protein Kinase C (PKC) family has been shown to regulate human melonogenesis through tyrosinase activation. Gene expression of tyrosinase, TRP-1 and TRP-2 is coordinated. All three enyzmes are expressed in human epidermis. In melanocytes co-cultured with keratinocytes, these transcripts are expressed at a ratio of 45:45:10, respectively. In melanocytes cultured alone, only TRP-1 transcripts are present, indicating that a keratinocyte-derived signal is involved in the coordinate expression of these genes. The regulation of keratinocyte-melanocyte interactions and the mechanism of melanosome transfer into keratinocytes are not yet understood.

The Protease-activated receptor-2 (PAR-2) is a seven transmembrane G-protein-coupled receptor, that is related to, but distinct from the thrombin receptors (TR, also named PAR-1, and PAR-3) in its sequence. Both receptors are activated proteolytically by an arginine-serine cleavage at the extracellular domain. The newly created N-termini then activate these receptors as tethered ligands. Both receptors could be activated by trypsin, but only the TRs are activated by thrombin. Only PAR-2 is activated by mast cell tryptase. Both receptors could also be activated by the peptides that correspond to their new N-termini, independent of receptor cleavage. SLIGRL, the mouse PAR-2 activating peptide, is equipotent in the activation of the human receptor. While the function of the TR is well documented, the biology of the PAR-2 has not yet been fully identified. A role for PAR-2 activation in the inhibition of keratinocyte growth and differentiation has been recently described (Derian et al., "Differential Regulation of Human Keratinocyte Growth and Differentiation by a Novel Family of Protease-activate Receptors", Cell Growth & Differentiation, Vol. 8, pp. 743–749, July 1997).

SUMMARY OF THE INVENTION

In accordance with this invention, we have found methods for affecting changes in mammalian skin pigmentation comprising topically applying to the skin of a mammal a compound which affects the PAR-2 pathway and a method for the prevention and/or treatment of immunomediated inflammatory diseases. The compositions of this invention may contain one or more compounds that act as trypsin, as tryptase, as serine protease or as PAR-2.agonists, for increase in pigmentation. Alternatively, they may contain one or more compounds that act as serine protease inhibitors, trypsin inhibitors, thrombin inhibitors, tryptase inhibitors, chymase inhibitors, as PAR-2 pathway inhibitors or PAR-2 antagonists for decrease in pigmentation, or "depigmentation". In addition, the compositions of this invention may contain one or more compounds that are inflammatory cell serine protease inhibitors that are useful for the prevention and/or treatment of immunomediated inflammatory diseases, especially those associated with the respiratory tract, such as asthma and allergic rhinitis.

As used herein, "mammal" means any member "of the higher vertebrate animals comprising the class "Mammalia", as defined in Webster's Medical Desk Dictionary 407 (1986), and includes but is not limited to humans. As used herein, "receptor" shall include both intracellullar and extracellular receptors and shall mean those molecules capable of receiving and transducing a signal. The term PAR-2 refers to the protease-activated receptor-2 or a related protease activated receptor. The Protease-activated receptor-2 (hereinafter, "PAR-2") is a serine-protease activated receptor that is expressed in numerous tissues, including keratinocytes and fibroblasts. The thrombin receptor (also named PAR-1, hereinafter, "TR") is a serine-protease activated receptor that is expressed in numerous tissues, including keratinocytes. The biological roles of PAR-2 and TR in skin are not entirely known. However, we have found that interactions between keratinocytes and melanocytes, via the PAR-2 pathway, affect melanogenesis. We have found that thrombin inhibitors, and/or tryptase inhibitors, and/or trypsin inhibitors and PAR-2 antagonists can be used as depigmenting agents without irritation of the skin. PAR-2 agonists and serine proteases such as trypsin and tryptase can be used as darkening agents. Furthermore, PAR-2 could be useful as a target for whitening and darkening agents.

BRIEF DESCRIPTION OF THE DRAWINGS

FIG. 1A is a graph depicting the increase or decrease in relative pigmentation of epidermal equivalents containing melanocytes treated with known pigmenting and depigmenting agents in accordance with the methods of this invention.

FIG. 1B is a graph depicting the increase or decrease in relative pigmentation in epidermal equivalents containing melanocytes treated in accordance with the methods and compositions of this invention.

FIG. 4A is a graph depicting the dose/response with respect to pigmentation in epidermal equivalents containing melanocytes when treated with compositions of this invention.

FIG. 5A is a photograph depicting gels showing the expression of TR and PAR-2 in skin, melanoma cells and epidermal equivalents containing melanocytes.

FIG. 5B is a photograph depicting gels showing the expression of TR and PAR-2 by primary human melanocytes.

FIGS. 6A and 6B are photographs depicting gels showing the expression of various genes after treatment with different concentrations of Compound I and SLIGRL.

FIG. 7 is a graph showing the effects of different compositions of this invention on the brightness of guinea pig nipple pigmentation.

FIGS. 11A, 11B and 11C are photographs of electron micrographic views of epidermal equivalents containing melanocytes treated with compositions of this invention.

DETAILED DESCRIPTION OF THE PREFERRED EMBODIMENTS

Skin Pigmentating and Depigmentating Agents

Figure 2:
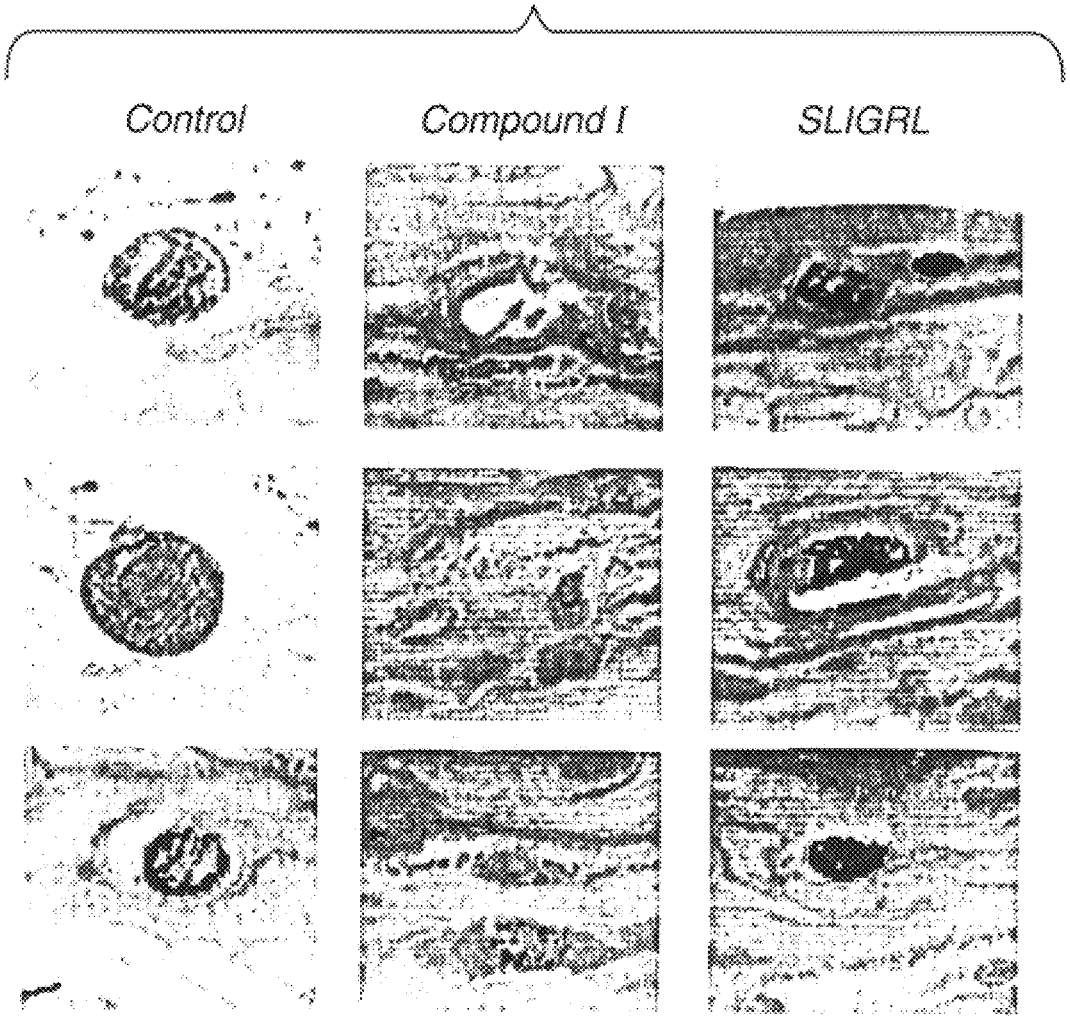
FIG. 2 is a group of images of epidermal equivalents containing melanocytes treated with PAR-2 agonists and Compound I.

We have discovered that trypsin, tryptase and PAR-2 agonists can be used to increase pigmentation and that trypsin inhibitors, and/or tryptase inhibitors, and/or thrombin inhibitors and PAR-2 antagonists act to decrease pigmentation in mammalian skin. The compounds described in U.S. Pat. No. 5,523,308, which is hereby incorporated herein by reference, and behave as thrombin and/or trypsin and/or tryptase inhibitors, are useful in methods of this invention. Some of these compounds are also described in Costanzo, et al., "Potent Thrombin Inhibitors That Probe the S. Subsite: Tripeptide Transition State Analogues Based on a Heterocycle-Activated Carbonyl Group", *J. Med. Chem.*, 1996, Vol. 39, pp. 3039–3043 and have the following structural formula 1:

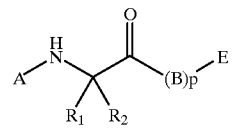

wherein:

A is selected from the group consisting of $C_{1-8}$alkyl, carboxy$C_{1-4}$alkyl, $C_{1-4}$alkoxycarbonyl$C_{1-4}$alkyl, phenyl$C_{1-4}$alkyl, substituted phenyl$C_{1-4}$alkyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), formyl, $C_{1-4}$alkoxycarbonyl, $C_{1-12}$alkylcarbonyl, phenyl$C_{1-4}$alkoxycarbonyl, $C_{3-7}$cycloalkylcarbonyl, phenylcarbonyl, substituted phenylcarbonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), $C_{1-4}$alkylsulfonyl, $C_{1-4}$alkoxysulfonyl, perfluoro$C_{1-4}$alkylsulfonyl, phenylsulfonyl, substituted phenylsulfonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 10-camphorsulfonyl, phenyl$C_{1-4}$alkylsulfonyl, substituted phenyl$C_{1-4}$alkylsulfonyl, $C_{1-4}$alkylsulfinyl, perfluoro$C_{1-4}$alkylsulfinyl, phenylsulfinyl, substituted phenylsulfinyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), phenyl$C_{1-4}$alkylsulfinyl, substituted phenyl$C_{1-4}$alkylsulfinyl, 1-naphthylsulfonyl, 2-naphthylsulfonyl or substituted naphthylsulfonyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, carboxy or $C_{1-4}$alkoxycarbonyl), 1-naphthylsulfinyl, 2-naphthylsulfinyl or substituted naphthylsulfinyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl);

a D or L amino acid which is coupled at its carboxy terminus to the nitrogen depicted in formula I and is selected from the group consisting of alanine, asparagine, 2-azetidinecarboxylic acid, glycine, N-$C_{1-8}$alkylglycine, proline, 1-amino-1-cyclo$C_{3-8}$alkylcarboxylic acid, thiazolidine-4-carboxylic acid, 5,5-dimethylthiazolidine-4-carboxylic acid, oxazolidine-4-carboxylic acid, pipecolinic acid, valine, methionine, cysteine, serine, threonine, norleucine, leucine, tert-leucine, isoleucine, phenylalanine, 1-naphthalanine, 2-naphthalanine, 2-thienylalanine, 3-thienylalanine, [1,2,3,4]-tetrahydroisoquinoline-1-carboxylic acid and [1,2,3,4]-tetrahydroisoquinoline-2-carboxylic acid where the amino terminus of said amino acid is connected to a member selected from the group consisting of $C_{1-4}$alkyl, tetrazol-5-yl-$C_{1-2}$alkyl, carboxy$C_{1-4}$alkyl, $C_{1-4}$alkoxycarbonyl$C_{1-4}$alkyl, phenyl$C_{1-4}$alkyl, substituted phenyl $C_{1-4}$alkyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1,1-diphenyl$C_{1-4}$alkyl, 3-phenyl-2-hydroxypropionyl, 2,2-diphenyl-1-hydroxyethylcarbonyl, [1,2,3,4]-tetrahydroisoquinoline-1-carbonyl, [1,2,3,4]-tetrahydroisoquinoline-3carbonyl, 1-methylamino-1-cyclohexanecarbonyl, 1-hydroxy-1-cyclohexanecarbonyl, 1-hydroxy-1-phenylacetyl, 1-cyclohexyl-1-hydroxyacetyl, 3-phenyl-2-hydroxypropionyl, 3,3-diphenyl-2-hydroxypropionyl, 3-cyclohexyl-2-hydroxypropionyl, formyl, $C_{1-4}$alkoxycarbonyl, $C_{1-12}$alkylcarbonyl, perfluoro$C_{1-4}$alkyl$C_{0-4}$alkylcarbonyl, phenyl$C_{1-4}$alkylcarbonyl, substituted phenyl$C_{1-4}$alkylcarbonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl) 1,1-diphenyl$C_{1-4}$alkylcarbonyl, substituted 1,1-diphenyl$C_{1-4}$alkylcarbonyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), perfluoro$C_{1-4}$alkylsulfonyl, $C_{1-4}$alkylsulfonyl, $C_{1-4}$alkoxysulfonyl, phenylsulfonyl, substituted phenylsulfonyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 10-camphorsulfonyl, phenyl$C_{1-4}$alkylsulfonyl, substituted phenyl$C_{1-4}$alkylsulfonyl, perfluoro$C_{1-4}$alkylsulfinyl, $C_{1-4}$alkylsulfinyl, phenyisulfinyl, substituted phenylsulfinyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), phenyl$C_{1-4}$alkylsulfinyl, substituted phenyl$C_{1-4}$alkylsulfinyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$-alkoxycarbonyl), 1-naphthylsulfonyl, 2-naphthylsulfonyl, substituted naphthylsulfonyl,(where the naphthyl substituents are independently selected from one or more of, $C_{1-4}$alkyl, perfluoro$C_{1-4}$alkyl, $C_{1-4}$-alkoxy, hydroxy, halo, amido, nitro, amino, $C_{1-4}$alkylamino, $C_{1-4}$dialkylamino, carboxy or $C_{1-4}$-alkoxycarbonyl), 1-naphthylsulfinyl, 2-naphthylsulfonyl, and substituted naphthylsulfinyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$-dialkylamino, carboxy or $C_{1-4}$alkoxycarbonyl); or a poly peptide comprised of two amino acids, where the first amino acid is a D or L amino acid, bound via its carboxy terminus to the nitrogen depicted in formula I and is selected from the group consisting of glycine, N-$C_{4-8}$alkylglycine, alanine, 2-azetidinecarboxylic acid, proline, thiazolidine-4-carboxylic acid, 5,5-dimethylthiazolidine-4-carboxylic acid, oxazolidine-4-carboxylic acid, 1-amino-1-cyclo$C_{3-8}$alkylcarboxylic acid, 3-hydroxyproline, 4-hydroxyproline, 3-($C_{1-4}$alkoxy)proline, 4-($C_{1-4}$alkoxy)proline, 3,4-dehydroproline, 2,2-dimethyl4-thiazolidine carboxylic acid, 2,2-dimethyl-4-oxazolidine carboxylic acid, pipecolinic acid, valine, methionine, cysteine, asparagine, serine, threonine, leucine, tert-leucine, isoleucine, phenylalanine, 1-naphthalanine, 2-naphthalanine, 2thienylalanine, 3-thienylalanine, [1,2,3,4]-tetrahydroisoquinoline-1-carboxylic acid, [1,2,3,4]-tetrahydroisoquinoline-2-carboxylic acid, aspartic acid4-$C_{1-4}$alkyl ester and glutamic acid-5-$C_{1-4}$alkyl ester and the second D or L amino acid, is bound to the amino terminus of said first amino acid, and is selected from the group consisting of phenylalanine, 4-benzoylphenylalanine, 4-carboxyphenylalanine, 4-(carboxy $C_{0-2}$alkyl) phenylalanine, substituted phenylalanine (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 3-benzothienylalanine, 4-biphenylalanine, homophenylalanine, octahydroindole-2-carboxylic acid, 2-pyridylalanine, 3-pyridylalanine, 4-thiazolyalanine, 2-thienylalanine, 3-(3-benzothienyl) alanine, 3-thienylalanine, tryptophan, tyrosine, asparagine, 3-tri-$C_{1-4}$alkylsilylalanine, cyclohexyglycine, diphenylglycine, phenylglycine, methionine sulfoxide, methionine sulfone, 2,2-dicyclohexylalanine, 2-(1-naphthylalanine), 2-(2-naphthylalanine), phenyl substituted phenylalanine (where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), aspartic acid, aspartic acid-4-$C_{1-4}$alkyl ester, glutamic acid, glutamic acid-5-$C_{1-4}$alkyl ester, cyclo$C_{3-8}$alkylalanine, substituted cyclo$C_{3-8}$alkylalanine (where the ring substituents are carboxy, $C_{1-4}$alkylcarboxy, $C_{1-4}$alkoxycarbonyl or aminocarbonyl), 2,2-diphenylalanine and all alpha-$C_{1-5}$alkyl of all amino acid derivatives thereof, where the amino terminus of said second amino acid is unsubstituted or monosubstituted with a member of the group consisting of formyl, $C_{1-12}$alkyl, tetrazol-5-yl$C_{1-2}$alkyl, carboxy$C_{1-8}$alkyl, carboalkoxy$C_{1-4}$alkyl, phenyl $C_{1-4}$alkyl, substituted phenyl$C_{1-4}$alkyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1,1-diphenyl$C_{1-4}$alkyl, $C_{1-6}$alkoxycarbonyl, phenyl$C_{1-6}$alkoxycarbonyl, $C_{1-12}$alkylcarbonyl, perfluoro$C_{1-4}$alkyl$C_{0-4}$alkylcarbonyl, phenyl$C_{1-4}$alkylcarbonyl, substituted phenyl$C_{1-4}$alkylcarbonyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1,1-diphenyl$C_{1-4}$alkylcarbonyl, $C_{1-4}$alkylsulfonyl, $C_{1-4}$alkoxysulfonyl, perfluoro$C_{1-4}$alkylsulfonyl, phenylsulfonyl, substituted phenylsufonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 10-camphorsulfonyl, phenyl$C_{1-4}$alkylsulfonyl, substituted phenyl$C_{1-4}$alkylsulfonyl, $C_{1-4}$alkylsulfinyl, perfluoro $C_{1-4}$alkylsulfinyl, phenylsulfinyl, substituted phenylsufinyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), phenyl$C_{1-4}$alkylsulfinyl, substituted phenyl$C_{1-4}$alkylsulfinyl 1-naphthylsulfonyl, 2-naphthylsulfonyl, substituted naphthylsulfonyl (where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1-naphthylsulfinyl, 2-naphthylsulfinyl and substituted naphthylsulfinyl (where the naphthyl substituent is selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl);

$R_1$ is selected from the group consisting of hydrogen and $C_{1-5}$alkyl;

$R_2$ is selected from the group consisting of amino$C_{2-5}$alkyl, guanidino$C_{2-5}$alkyl, $C_{1-4}$alkylguanidino$C_{2-5}$alkyl, di$C_{1-4}$alkylguanidino$C_{2-5}$alkyl, amidino$C_{2-5}$alkyl, $C_{1-4}$alkylamidino$C_{2-5}$alkyl, di$C_{1-4}$alkylamidino$C_{2-5}$alkyl, $C_{1-3}$alkoxy $C_{2-5}$alkyl, phenyl, substituted phenyl (where the substituents are independently selected from one or more of, amino, amidino, guanidino, $C_{1-4}$alkylamino, $C_{1-4}$dialkylamino, halogen, perfluoro $C_{1-4}$alkyl, $C_{1-4}$alkyl, $C_{1-3}$alkoxy or nitro), benzyl, phenyl substituted benzyl (where the substituents are independently selected from one or more of, amino, amidino, guanidino, $C_{1-4}$alkylamino, $C_{1-4}$dialkylamino, halogen, perfluoro $C_{1-4}$alkyl, $C_{1-4}$alkyl, $C_{1-3}$alkoxy or nitro), hydroxy$C_{2-5}$alkyl, $C_{1-5}$alkylamino$C_{2-5}$alkyl, $C_{1-5}$dialkylamino$C_{2-5}$alkyl, 4-aminocyclohexyl$C_{0-2}$alkyl and $C_{1-5}$alkyl;

p is 0 or 1;

B is

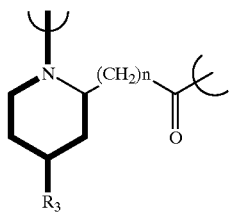

where n is 0–3, R3 is H or $C_{1-5}$alkyl and the carbonyl moiety of B is bound to E;

E is a heterocycle selected from the group consisting of oxazolin-2-yl, oxazol-2-yl, thiazol-2-yl, thiazol-5-yl, thiazol-4-yl, thiazolin-2-yl, imidazol-2-yl, 4-oxo-2-quinoxalin-2-yl, 2-pyridyl, 3-pyridyl, benzo[b]thiophen-2-yl, benzoxazol-2-yl, benzimidazol-2-yl, benzothiazol-2-yl, triazol-4-yl, triazol-6-yl, tetrazol-2-yl, pyrimidin-2-yl, quinolin-2-yl, indol-2-yl, pyrazol-2-yl, 4,5,6,7-tetrahydrobenzothiazol-2-yl, naphtho[2,1-d]thiazol-2-yl, naphtho[1,2-d]thiazol-2-yl quinoxalin-2-yl, isoquinolin-1-yl, isoquinolin-3-yl, benzo[b]furan-2-yl, pyrazin-2-yl, quinazolin-2-yl, isothiazol-5-yl, isothiazol-3-yl, purin-8-yl and a substituted heterocycle where the substituents are selected selected from $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy, $C_{1-4}$alkoxycarbonyl, hydroxy or phenyl$C_{1-4}$alkylaminocarbonyl; or pharmaceutically acceptable salts thereof.

More particularly, in our opinion, some of the compounds of the foregoing formula containing a D-phenylalanine-proline-arginine motif should be effective in inhibiting the PAR-2 pathway and causing depigmentation. One particularly preferred compound which acts as a thrombin, trypsin and tryptase inhibitor and is active in depigmenting mammalian skin is (S)N-Methyl-D-phenylalanyl-N-[4-[(aminoiminomethyl)amino]-1-(2-benzothiazolylcarbonyl)butyl]-L-prolinamide (Chemical Abstracts name) (hereinafter referred to as "Compound I"). Other compounds which are analogs or function similarly to Compound I and are set forth in U.S. Pat. No. 5,523,308 are active in the methods and compositions of this invention. Other compounds that inhibit trypsin, such as serine protease inhibitors, and in particular, soybean trypsin inhibitor (STI) will also be useful in methods of this invention. Soybean, limabean and blackbean extracts, and other natural products made from these beans, such as, but not limited to, bean milk, bean paste, miso and the like, also serve to reduce pigmentation by the PAR-2 pathway.

Additional sources of serine protease inhibitors may be extracted from the species belonging to the following plant families: Solanaceae (e.g., potato, tomato, tomatilla, and the like); Gramineae (e.g., rice, buckwheat, sorghum, wheat, barley, oats and the like); Cucurbitaceae (e.g., cucumbers, squash, gourd, luffa and the like); and, preferably, Leguminosae (e.g., beans, peas, lentils, peanuts, and the like).

While not willing to be bound by the following theory, we theorize that the compounds capable of affecting the pigmentation of the skin do so by interacting directly or indirectly with the keratinocyte PAR-2 or with its activating protease, and thereby affect melanogenesis, directly or indirectly. Possibly, the compounds of this invention induce, in the case of increased pigmentation or reduce, in the case of decreased pigmentation, the signal to transport melanosomes by melanocytes, or to receive melanosomes by keratinocytes in the skin.

The compounds which are active in the compositions and methods of this invention may be delivered topically by any means known to those of skill in the art. If the delivery parameters of the topically active pharmaceutical or cosmetic agent so require, the topically active composition of this invention may preferably be further composed of a pharmaceutically or cosmetically acceptable vehicle capable of functioning as a delivery system to enable the penetration of the topically active agent into the skin.

One acceptable vehicle for topical delivery of some of the compositions of this invention, particularly proteins such as trypsin and STI, may contain liposomes. The liposomes are more preferably non-ionic and contain a) glycerol dilaurate (preferably in an amount of between about 5% and about 70% by weight); b) compounds having the steroid backbone found in cholesterol (preferably in an amount of between about 5% and about 45% by weight); and c) one or more fatty acid ethers having from about 12 to about 18 carbon atoms (preferably in an amount of between about 5% and about 70% by weight collectively), wherein the constituent compounds of the liposomes are preferably in a ratio of about 37.5:12.5:33.3:16.7. Liposomes comprised of glycerol dilaurate/cholesterol polyoxyethylene-10-stearyl ether/polyoxyethylene-9-lauryl ether (GDL liposomes) are most preferred. Preferably the liposomes are present in an amount, based upon the total volume of the composition, of from about 10 mg/mL to about 100 mg/mL, and more preferably from about 20 mg/mL to about 50 mg/mL. A ratio of about 37.5:12.5:33.3:16.7 is most preferred. Suitable liposomes may preferably be prepared in accordance with the protocol set forth in Example 1, though other methods commonly used in the art are also acceptable. The above described composition may be prepared by combining the desired components in a suitable container and mixing them under ambient conditions in any conventional high shear mixing means well known in the art for non-ionic liposomes preparations, such as those disclosed in Niemiec et al., "Influence of Nonionic Liposomal Composition On Topical Delivery of Peptide Drugs Into Pilosebacious Units: An In Vivo Study Using the Hamster Ear Model," 12 Pharm. Res. 118488 (1995) ("Niemiec"), which is incorporated by reference herein in its entirety. We have found that the presence of these liposomes in the compositions of this invention may enhance the depigmenting capabilities of some of the compositions of this invention.

Other preferable formulations may contain, for example, soybean milk or other liquid formulations derived directly from legumes or other suitable plant. For example, such a formulation may contain a large proportion of soybean milk, an emulsifier that maintains the physical stability of the soybean milk, and, optionally a chelating agent, preservatives, emollients, humectants and/or thickeners or gelling agents.

Oil-in-water emulsions, water-in-oil emulsions, solvent-based formulations and aqueous gels known to those of skill in the art may also be utilized as vehicles for the delivery of the compositions of this invention.

The source of active compound to be formulated will generally depend upon the particular form of the compound. Small organic molecules and peptidyl fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

In alternative embodiments, the topically active pharmaceutical or cosmetic composition may be optionally combined with other ingredients such as moisturizers, cosmetic adjuvants, anti-oxidants, bleaching agents, tyrosinase inhibitors and other known depigmentation agents, surfactants, foaming agents, conditioners, humectants, fragrances, viscosifiers, buffering agents, preservatives, sunscreens and the like. The compositions of this invention may also contain active amounts of retinoids (i.e., compounds that bind to any members of the family of retinoid receptors), including, for example, tretinoin, retinol, esters of tretinoin and/or retinol and the like.

The topically active pharmaceutical or cosmetic composition should be applied in an amount effective to affect changes in the pigmentation of mammalian skin. As used herein "amount effective" shall mean an amount sufficient to cover the region of skin surface where a change in pigmentation is desired. Preferably, the composition is liberally applied to the skin surface such that, based upon a square cm of skin surface, from about 2 $\mu$l /cm$^2$ to about 200 $\mu$l/cm$^2$ of topically active agent is present when a change in pigmentation is desired. When using a thrombin and trypsin inhibitor such as Compound I or its analogs, whether synthetically- or naturally-derived in a formulation, such an active compound should be present in the amount of from about 0.0001% to about 15% by weight/volume of the composition. More preferably, it should be present in an amount from about 0.0005% to about 5% of the composition; most preferably, it should be present in an amount of from about 0.001% to about 1% of the composition. Of course, these ranges are suggested for the foregoing components. The lower set of ranges is intended to be efficacious for PAR-2 pathway agonists/antagonists and/or inhibitors having high therapeutic indices and which do not require significantly larger concentrations or doses to be effective in the methods of this invention. Such compounds may be synthetically- or naturally-derived.

Liquid derivatives and natural extracts made directly from plants or botanical sources may be employed in the compositions of this invention in a concentration (w/v) from about 1 to about 99%. Fractions of natural extracts and naturally-derived protease inhibitors such as STI may have a different preferred range, from about 0.01% to about 20% and, more preferably, from about 1% to about 10% of the composition. Of course, mixtures of the active agents of this invention may be combined and used together in the same formulation, or in serial applications of different formulations.

We have unexpectedly found that when topically active agents, such as PAR-2 agonists and/or inhibitors and trypsin and/or thrombin and/or tryptase and/or their inhibitors, are topically applied to an animal's skin, a significant change in pigmentation was achieved. Preferably, depigmenting agents (as well as other pigmentation-affecting agents of this invention) are applied to the skin of a mammal at a relatively high concentration and dose (from about 0.005% to about 1% for compounds having high therapeutic indices such as Compound I and related compounds; from about 20% to about 99% for liquid derivatives and extracts of botanical materials; and from about 1% to about 20% for fractions of natural extracts and naturally-derived protease inhibitors such as STI or mixtures thereof) between one and two times daily for a period of time until the skin evidences a change in pigmentation. This may be for from about four to about ten weeks or more. Thereafter, once the change in pigmentation has been achieved, a lower concentration and dose (from about 0.00001% to about 0.005% for compounds having high therapeutic indices such as Compound I and related compounds; from about 10% to about 90% for liquid derivatives and extracts of botanical materials; and from about 0.01% to about 5% for fractions of natural extracts and naturally-derived protease inhibitors such as STI or mixtures thereof), of active ingredient may be applied on a less frequent time schedule, e.g., about once per day to about twice per week. The effects of the active agents of this invention are reversible, therefore, in order to maintain these effects, continuous application or administration should be performed. The invention illustratively disclosed herein suitably may be practiced in the absence of any component, ingredient, or step which is not specifically disclosed herein.

The invention illustratively disclosed herein suitably may be practiced in the absence of any component, ingredient, or step which is not specifically disclosed herein. Several examples are set forth below to further illustrate the nature of the invention and the manner of carrying it out, but do not serve to limit the scope of the methods and compositions of this invention.

EXAMPLE 1

Protease Inhibitors Affect Pigmentation

In order to study the possible roles of the PAR-2 pathway in pigmentation, an in vitro epidermal equivalent system was used. The epidermal equivalent system used contained melanocytes. One epidermal equivalent system which is useful in performing this study is the MelanoDerm system, available commercially from MatTek Co. This system contains human normal melanocytes, together with normal, human-derived epidermal keratinocytes, which have been cultured to form a multi-layered, highly differentiated model of the human epidermis. In the following examples, equivalents were treated with test compounds for three days and samples were harvested on the fourth day after beginning of treatment. The harvested equivalents were stained with DOPA (a substrate for tyrosinase) and H&E (a standard histological stain) or with Fontana-Mason (F&M) staining, another stain known to those of skill in the art. F&M staining is a silver staining technique that clearly and cleanly marks melanins which have high silver nitrate reducing activity. Multilayered human epidermal equivalents containing melanocytes were used as an in vitro model system to study the effect of protease inhibitors on melanogenesis. Epidermal equivalents used were commercially available as Melano-Derm from MatTek of Ashland, Mass. These equivalents are known to respond to ultraviolet B ("UVB") irradiation and known whitening agents such as benzaldehyde and hydroquinone by increasing and reducing pigmentation, respectively. The MelanoDerm epidermal equivalents were exposed to benzaldehyde (available from Sigma of St. Louis, Mo.), hydroquinone (available from Sigma) and UVB irradiation. UV irradiation was performed with a UVB FS light source in an exposure chamber, with plate covers removed and Phosphate-buffered saline (PBS, from Gibco-BRL, Gaithersburg, Md.) present in the lower chamber. UVB intensity was measured with a UVX radiometer (UVP Inc., San Gabriel, Calif.). Equivalents were treated with 0.1–0.12 J/cm$^2$ No loss of viability was observed in equivalents treated with up to 0.3 J/cm$^2$.

On the fourth day of exposure to the test compounds/ultraviolet irradiation, the equivalents were fixed, sectioned and stained, or stained as whole without sectioning. MelanoDerm equivalents were formalin fixed and put in paraffin blocks, and sections from the MelanoDerm equivalents were stained in accordance with the following standard procedures: (1) H&E, (2) DOPA+H&E and (3) Fontana-Mason ("F&M") using standard techniques known to those of skill in the art. Alternatively, whole MelanoDerm equivalents were stained and their images were captured for image analysis. At least three sections per equivalent, three equivalents per experiment were processed. Each experiment was repeated three time. DOPA is a substrate for tyrosinase. F&M identifies silver nitrate reducing molecules, which identifies primarily melanins. F&M stained sections were used for image analysis using Optomax Image Analysis Systems, from Optomax Inc., Hollis, N.H. Alternatively, Empire Images database 1.1 was used on a Gateway 2000 P5-100 computer (Media Cybemetics, Silver Springs, Md.) for capturing images. Image Pro Plus version 4.0 was used for image analysis. Parameters measured were as follows: (1) level of pigmentation within individual melanocytes and (2) number of pigmented melanocytes per field, for the Optomax system, or (1) the surface area of silver deposits within melanocytes and (2) the number of pigmented melanocytes for the Image Pro system. Using the Optomax system, surface area of silver deposits within individual melanocytes was measured in 60 melanocytes, using multiple sections from triplicate equivalents per treatment. The number of melanocytes per field was calculated in these sections. A "pigmentation factor" was defined as the average surface area of silver deposits within an individual melanocyte, multiplied by the number of pigmented melanocytes per field. A value of one was assigned to untreated controls, and values of treatment groups were normalized to their relevant controls. Using the Image Pro system, surface area of silver nitrate deposits and number of melanocytes were measured for whole equivalents. A value of one was assigned to untreated controls and values of treatment groups were normalized to their relevant controls.

FIG. 1A is a graph depicting the increase or decrease in relative pigmentation, as measured and calculated by the whole equivalent/lmage Pro system, as set forth above, when exposed to benzaldehyde (50 µM), hydroquinone (50 µM) and UVB irradiation (0.12 J/cm$^2$).

The human epidermal equivalents were also exposed to mixtures of protease inhibitors, said protease inhibitors are set forth in Table A below. The protease inhibitors were available from Boehringer Mannheim of Indianapolis, Ind.. Complete® Protease Inhibitor Cocktail tablets available from Boehringer Mannheim were used, containing inhibitors of chymotrypsin, thermolysin, papain, pronase, pancreatic extract and trypsin. Soybean trypsin inhibitor ("STI") was available from Sigma and was dissolved in a 50 mg/ml liposome vehicle or in 1x PBS. All other protease inhibitors used in this in vitro example were dissolved in 1xPBS. GDL liposomes were prepared as set forth in Niemic, et al., above, with the exception of the following changes: the non-ionic liposomal formulation contained glycerol dilaurate (Emulsynt GDL, ISP Van Dyk)/cholesterol (Croda)/polyoxyethylene-10-stearyl ether (Brij76, ICI)/polyoxyethylene-9-lauryl ether, as at ratio of 37.5:12.5:33.3:16.7. Hepes buffer, 0.05M, pH 7.4 (Gibco-BRL of Gaithersburg, Md.) was used as the aqueous phase in the preparation of the liposomes. These mixtures of protease inhibitors and different combinations of serine protease inhibitors were tested for their ability to affect melanogenesis. As set forth in FIG. 1B, some of the serine protease inhibitors, particularly STI (soybean trypsin inhibitor), were very effective in inhibiting melanogenesis.

TABLE A

| Test Formulation | Ingredients |
| --- | --- |
| Complete ® | Total protease inhibitor mixture - x25 |
| Mix-1 | Serine Protease inhibitors - 90 μg/mL Phenylmethyl-sulfonyl fluoride ("PMSF") and 50 μg/mL L-1-Chloro-3-[4-tosylamido]-4-phenyl-2-butanone ("TPCK") |
| Mix-2 | Serine protease inhibitors - 0.1 μg/mL aprotinin, 50 μg/mL Soybean trypsin inhibitor ("STI"), 0.5 μg/mL leupeptin and 0.25 μg/mL (L-1-Chloro-3-[4-tosylamido]-7-amino-2-heptanone-HCl) ("TLCK") |
| STI | Soybean trypsin inhibitor - 1 mg/ml |

EXAMPLE 2

A Protease-activated Receptor Is Involved In Pigmentation

Example 1 demonstrates that STI reduces pigmentation. STI inhibits trypsin. Because trypsin is known to activate TR and PAR-2, we tested the possible involvement of TR and PAR-2 in pigmentation. MelanoDerm human epidermal equivalents were treated with the TR and PAR-2 agonists and antagonists set forth in Table B below daily for three days. On the fourth day, the samples were harvested, fixed, and DOPA, H&E or F&M staining was performed. Histological and whole-equivalent examination revealed changes in pigmentation following the treatments. FIG. 2 depicts the results of this example. As shown therein, the PAR-2 peptide agonist SLIGRL induced pigmentation in individual melanocytes. Treatment with Compound I, an inhibitor of thrombin and trypsin, resulted in decreased pigmentation.

Figure 3:
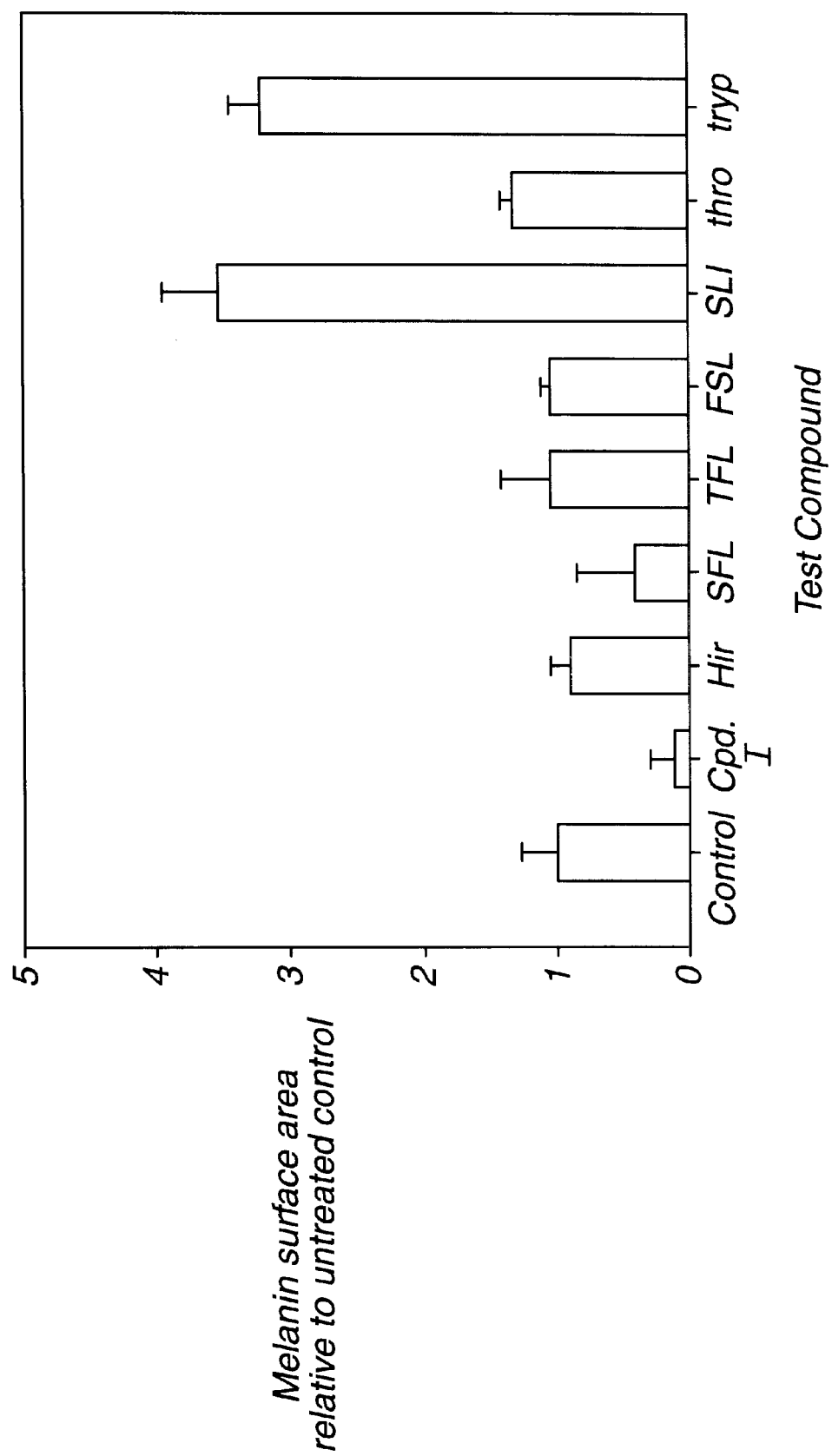
FIG. 3 is a graph depicting the increase or decrease in relative pigmentation in epidermal equivalents containing melanocytes treated in accordance with the methods and compositions of this invention.

FIG. 3 shows the results of the studies set forth in this example, representing the level of pigmentation in Melano-Derm equivalents treated with TR and PAR-2 reagents. SLIGRL, a PAR-2 agonist, dramatically increased pigmentation, indicating that PAR-2 might be involved in pigmentation. Hirudin, a thrombin-specific inhibitor, and TFLLRNPNDK, a TR selective agonist had no effect on pigmentation. However, SFLLRN, a less specific TR agonists, showed a trend of lightening or reducing pigmentation. This indicates that TR is less likely to be involved in pigmentation.

TABLE B

| TR and PAR-2 Reagents | Description |
| --- | --- |
| Thrombin | Activates TR |
| Trypsin | Activates TR and PAR-2 |
| TFLLRNPNDK | TR peptide agonist - activates TR only |
| SLIGRL | PAR-2 peptide agonist - activates PAR-2 only |
| SFLLRN | TR peptide agonist - activates TR, TR, cross-reacts with PAR-2 |
| FSLLRN | Scrambled peptide - inactive |
| Hirudin | Specific inhibitor of thrombin |
| Compound I | Thrombin and trypsin inhibitor |

EXAMPLE 3

Figure 4B:
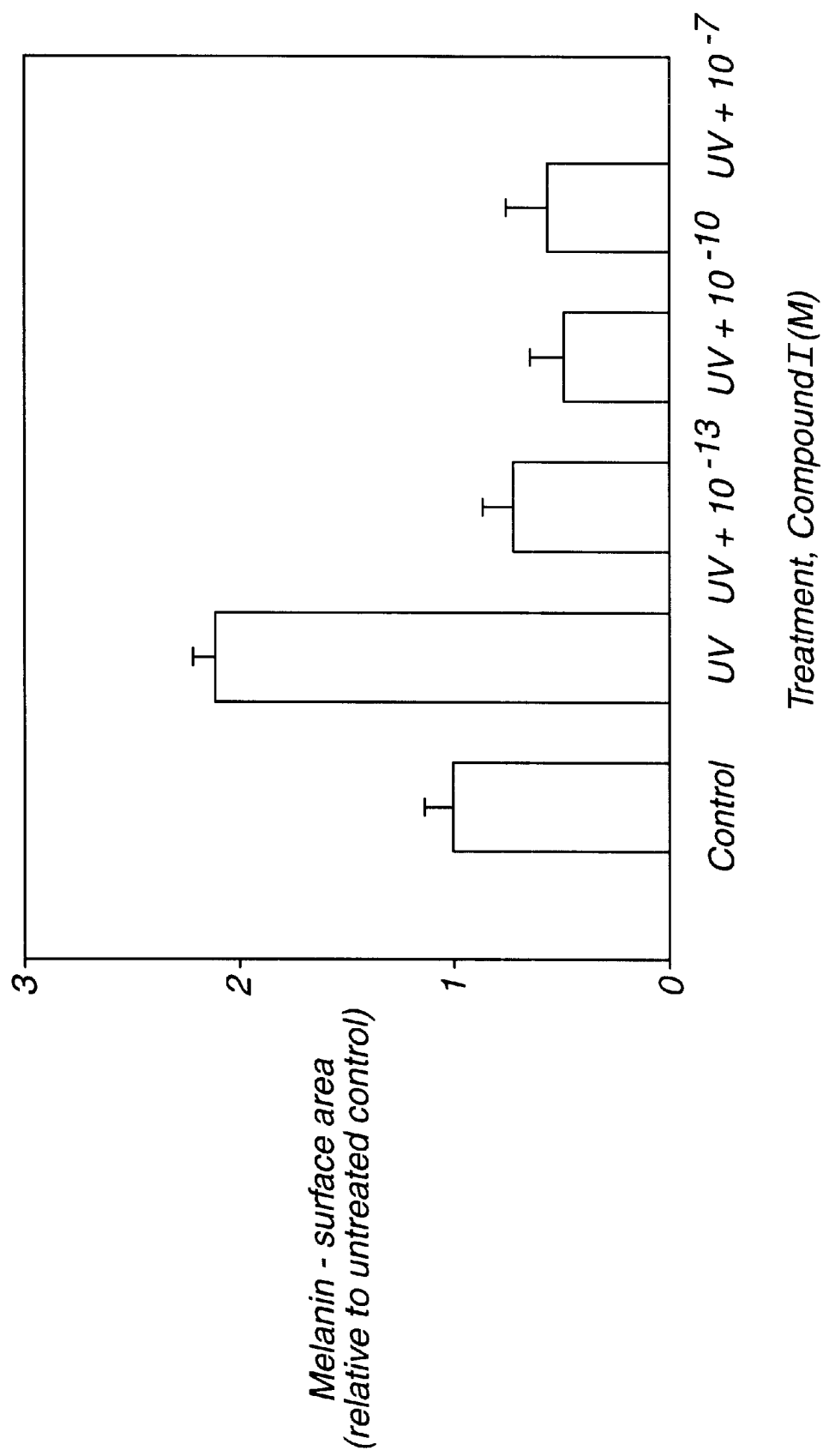
FIG. 4B is a graph depicting the response of epidermal equivalents containing melanocytes after exposure to ultraviolet light followed by treatment with compositions of this invention.

A Dose-response Relation Between Protease-activated Receptors Signaling and Melanogenesis MelanoDerm equivalents were treated with increasing concentrations of SLIGRL, the PAR-2 peptide agonist, at 0, 10 and 50 μM in the same manner as set forth in Example 2. F&M staining was performed in the fourth day. As shown in FIG. 4A, increasing concentrations of SLIGRL, the PAR-2 activator, result in increased pigmentation. Trypsin, a PAR-2 activator, has the same effect Treatment with increasing concentrations of Compound I, the thrombin and trypsin inhibitor, from 0.1 μM to 1 μM resulted in decreasing pigmentation (see FIG. 4A). Pretreatment of the equivalents with UVB irradiation increased melanogenesis, relative to untreated controls. Compound I was able to reduce this UVB-induced pigmentation as well (FIG. 4B). This example demonstrates a dose-response relation for increasing and decreasing pigmentation with the modulation of PAR-2 signaling. This example also demonstrates that Compound I can inhibit pigmentation and prevent UV-induced pigmentation.

EXAMPLE 4

PAR-2 is Expressed in Keratinocytes, But Not In Melanocytes

PAR-2 and TR expression have been demonstrated previously in keratinocytes and fibroblasts. This example demonstrates that PAR-2 is expressed in keratinocytes, but not in melanocytes. Furthermore, it demonstrates that TR is expressed in both keratinocytes and melanocytes. In order to demonstrate this, MelanoDerm human epidermal equivalents, human primary melanocyte cultures (neonatal and adult, from Clonetics of San Diego, Calif.) and Cloudman S91 mouse melanoma cells from ATCC of Rockville, Md. were grown in culture and total RNAs were extracted using "RNA Stat-60" reagent available from "Tel-Test B", Incorporated as described in Chomczymski, "Single Step Method of RNA Isolation by Acid Guanidinium Thiocyanate-phenol-chloroform extraction," 162 Anal. Biochem. 15669 (1987). A sufficient amount of RNase-free DNase available from Promega Corporation under the tradename "RQ1 RNase-free DNase" was then added to the extracted RNA from each sample such that each respective product will yield 200 ng of DNased-RNA using the procedure set forth in "RNase-free DNase", protocol published by Promega Corporation (May, 1995). The resulting 200 ng of DNased-RNA was reverse transcribed ("RT") via the procedure set forth in "Superscript II Reverse Transcriptase" a protocol published by Gibco-BRL (now Life Technologies, Incorporated) (April 1992), using random hexamers such as the random primers which are commercially available from Life Technologies, Incorporated.

The resulting RT products were then amplified via polymerase chain reaction ("PCR") using about a 0.5 unit (per 100 μl reaction) of a thermostable DNA polymerase which is commercially available from Perkin-Elmer-Cetus Corporation under the tradename "Taq polymerase" and about 0.1 μmol/reaction of TR and PAR-2 specific primers as described in Table C and in Marthinuss et al., 1995 which is hereby incorporated herein by reference or of glyceraldehyde-3-phosphate-dehydrogenase (G3PDH) primers, available from Clontech Laboratories, Inc. of Palo Alto, Calif. in accordance with the procedures set forth in Marthinuss et al., 1995 or in the protocol accompanying the primers from Clontech Laboratories.

The PCR products were then analyzed using 2% agarose/ethidium bromide gels according to methods well-known in the art in order to compare the level of expression of certain genes in keratinocytes and melanocytes. When necessary for better visualization, the resulting PCR products were precipitated with ethanol according to well-known procedures. When primers for G3PDH were used, only 10% of the PCR reaction products were used. An RNA sample from epidermal equivalents that was not reverse-transcribed was used as a negative control for each PCR amplification. The lack of genomic DNA contaminants was indicated by the lack of a band on the relevant lanes in the gels. A human skin RNA sample which was reverse-transcribed was used as a positive control when commercial positive controls were not available. The migration of the RT-PCR products on the gels was always identical to that of the positive controls, and to that of the reported amplimer sizes.

The relative quality of each respective RT-PCR reaction product was then compared by analyzing the mRNA level of G3PDH, a "housekeeping" gene, in each respective product. As illustrated in FIG. 5 and 6, G3PDH gene expression was found to be similar at all the time points examined, which thereby enabled the comparison of the relative levels of gene expression for the desired genes.

FIG. 5A shows that, as expected, TR and PAR-2 are expressed in total skin and in the MelanoDerm equivalents ("MD"). However, S91 melanoma cells ("S91") did not express PAR-2 or TR. To investigate this further, we tested primary newborn ("mel-NB") and adult ("mel-A") melanocytes for TR and PAR-2 expression. As shown in FIG. 5B, primary human melanocytes express TR but not PAR-2.

Therefore, we suggest that PAR-2 agonists and antagonists can interact with keratinocytes, but not with melanocytes, in the MelanoDerm equivalents, and that TR agonists and antagonists could interact with both keratinocytes and melanocytes. A keratinocyte-melanocyte interaction is, therefore, suggested, during which the keratinocyte-PAR-2 signal is converted into a pigmentation end-point.

Table C illustrates some of the DNA primers used, the amount of $MgCl_2$ required for the PCR reaction, and the length of the PCR cycle.

TABLE C

DNA Primers Utilized in RT-PCR Assay

| Primer (See attached Sequence Listing) | Amt. of $MgCl_2$ (mM) | Cycle (min) @ ° C. | No. of cycles | DNA Seq. ID No. |
|---|---|---|---|---|
| Tyrosinase sense TCAGCCCAGC ATCCTTCTTC | 1.25 | 1 @ 94<br>2 @ 55<br>3 @ 72 | 35 | 1 |
| Tyrosinase antisense CAGCCATTGT TCAAAAATAC-TGTCC | 1.25 | 1 @ 94<br>2 @ 55<br>3 @ 72 | 35 | 2 |
| TRP-1 sense 5'CCACTCTAATAAGCCCAAAC | 2.5 | 1 @ 94<br>2 @ 55<br>3 @ 72 | 35 | 3 |
| TRP-1 antisense 5'CTCAGCCATTCATCAAAGAC | 2.5 | 1 @ 94<br>2 @ 55<br>3 @ 72 | 35 | 4 |
| TRP-2 sense 5'AAAAGACATACGAGATTGCC | 2.5 | 1 @ 94<br>2 @ 55<br>3 @ 72 | 35 | 5 |
| TRP-2 antisense 5'CACAAAAAGACCAACCAAAG | 2.5 | 1 @ 94<br>2 @ 55<br>3 @ 72 | 35 | 6 |
| Trypsin sense 5'ATCC/TACTCCTGATCCTTACC | 2.5 | 1 @ 94<br>2 @ 45<br>3 @ 72 | 35 | 7 |
| Trypsin antisense 5'TGTCATTGTT/CCAGAGTCT/-CT/GC/GC | 2.5 | 1 @ 94<br>2 @ 45<br>3 @ 72 | 35 | 8 |
| PAR-2 sense - GGGAAAGGGGTTGGGGTAGAA-CCAGGCTTTTCC (5') | 2.5 | .5 @ 94<br>1 @ 55<br>3 @ 72 | 30 | 9 |
| PAR-2 antisense - GGCCAACGGCGATGTTTGCCTT-CTTCCTGGGG (3') | 2.5 | .5 @ 94<br>1 @ 55<br>3 @ 72 | 30 | 10 |
| TR-sense - CCTCTGAGTGCCAGAGGTACG-TCTACAG (5') | 2.5 | .5 @ 94<br>1 @ 55<br>3 @ 72 | 30 | 11 |
| TR-antisense - CCTAAGTTAACAGCTTTTTGTAT-ATGCTGTTATTCAGG (3') | 2.5 | .5 @ 94<br>1 @ 55<br>3 @ 72 | 30 | 12 |
| Thrombin-sense - AACCTGAAGGAGACGTGGAC (3') | 2.5 | .5 @ 94<br>1 @ 55<br>3 @ 72 | 35 | 13 |
| Thrombin-antisense - CAGGAGCCCAGAATATGAGTG (5') | 2.5 | .5 @ 94<br>1 @ 55<br>3 @ 72 | 35 | 14 |

EXAMPLE 5:

Keratinocyte-Melanocyte Contact is Required for Compound I Depigmenting Effect

The results of Example 4 suggest that melanocytes alone might not respond to the depigmenting effect of PAR-2 antagonists. Indeed, the level of pigmentation of human primary melanocytes or choleratoxin-induced S91 cells, which is reduced by hydroquinone and benzaldehyde, was not affected by Compound I.

Since PAR-2 is not expressed in melanocytes, we tested the possible requirement of keratinocyte-melanocyte interactions for the depigmenting effect of Compound I. Primary melanocyte cultures were compared to identical cultures plated under epidermal equivalents (EpiDerm, lacking melanocytes) to create a co-culture with no contact between keratinocytes and melanocytes. These were also compared to MelanoDerm equivalents, where melanocytes are present in the basal layer of the equivalent. Cultures were treated for three days with Compound I, with the PAR-2 agonist SLIGRL, and with the TR agonist TFLLRNPNDK, as set forth in Table D, and DOPA stained on the fourth day. In Table D, keratinocytes are indicated by "K", melanocytes are indicated by "M" and lack of keratinocyte-melanocyte contact is indicated as "no K-M contact". As shown in Table D, no effect on pigmentation was observed in primary melanocytes and in co-cultures treated with these agents. In MelanoDerm equivalents, compound I reduced and SLIGRL induced pigmentation, while TFLLRNPNDK had no effect. These results demonstrate that keratinocyte-melanocyte contact is required for the PAR-2 effect on pigmentation.

TABLE D

| Treatment | Melanocytes (no K) | Co-cultures (no K-M contact) | MelanoDerm (K-M contact) |
| --- | --- | --- | --- |
| Compound I | no effect | no effect | lightening |
| SLIGRL | no effect | no effect | darkening |
| TFLLRNPNDK | no effect | no effect | no effect |

EXAMPLE 6

Compound I Affects Melanocyte Gene Expression

MelanoDerm equivalents were treated with increasing concentrations of the thrombin and trypsin inhibitor, Compound I, or with increasing concentrations of the PAR-2 agonist SLIGRL. RNAs extracted from untreated and Compound I-treated equivalents were analyzed for gene expression by RT-PCR in the manner set forth above in Example 4. Gene-specific primers were designed as set forth in Table C above, and Clontech primers for human G3PDH were used as in Example 4. Melanogenic genes tested for expression level were tyrosinase, TRP-1, and TRP-2.

Figure 6A:
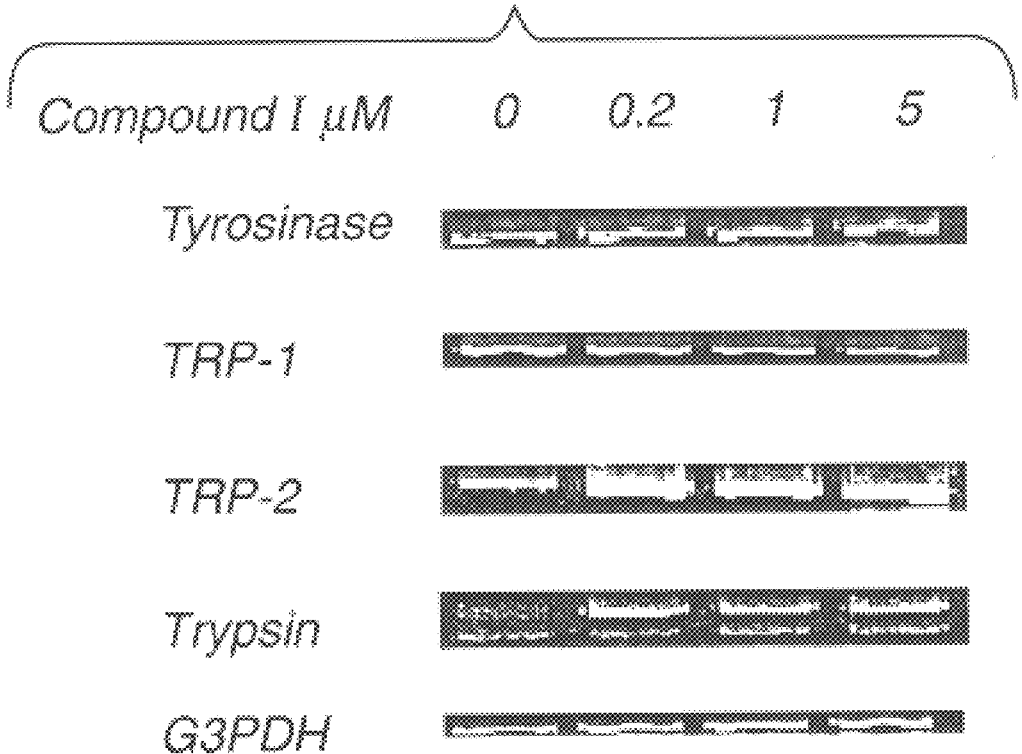

A dose-dependent decrease in TRP-1 and a dose-dependent increase in TRP-2 mRNA levels were observed in Compound I-treated samples, as shown in FIG. 6A. Tyrosinase expression, however, was not affected. These changes correlated with the dose-dependent whitening effect of this inhibitor. Both patterns of gene expression result in a lightening effect. TRP-2 enzyme processes dopaquinone to 5,6-dihydroxyindole carboxylic acid (DHICA), rather than to 5,6-dihydroxyindole (DHI). This process results in brown, finely dispersed eumelanin, as opposed to insoluble black eumelanin, and results in a lighter skin tone. TRP-1 stabilizes the melanogenic complex, enabling pigment production. Reduced levels of TRP-1 result in reduced tyrosinase activity and reduced pigmentation. Lack of this protein results in albinism. Increasing concentrations of SLIGRL, however, did not affect melanogenic gene expression (FIG. 6B).

TRP-1 and TRP-2 are melanocyte-specific. Compound I inhibits trypsin and thrombin. Hirudin, a specific thrombin inhibitor, had no effect on pigmentation, as seen above in Example 2. Thus, we decided to test whether trypsin and thrombin are expressed in skin. A probe designed to detect both brain and gastric trypsins, as described in Table C, detected the expression of both mRNAs in a total skin mRNA sample available from Invitrogen of Carlsbad, Calif., as well as in MelanoDerm equivalents. The same expression pattern was detected for thrombin. Both trypsin and thrombin were not expressed in normal melanocytes (FIGS. 5A, B). These data suggest that if trypsin activates PAR-2, it could be produced by the keratinocytes only. As shown in FIG. 6A, treatment with Compound I resulted in increased expression of trypsin. SLIGRL, which did not affect melanogenesis gene expression (FIG. 6B) also increased trypsin expression in the equivalents. We conclude that while trypsin is a possible natural activator of PAR-2 in skin and possibly affects pigmentation, its mRNA levels do not correlate with pigmentation. This suggests that another, yet unidentified serine protease, which is inhibited by compound 1, STI and the like, is the natural activator of PAR-2 in the epidermis. Compounds that induce or inhibit this protease would serve as darkening and lightening agents, respectively.

EXAMPLE 7

Thrombin and Trypsin Inhibitors and PAR-2 Agonists Affect Pigmentation In Vivo

Two guinea pigs were treated twice daily, five days/week for seven weeks with Compound I at 1 and 10 $\mu$M in 70:30 ethanol:propylene glycol vehicle on one pigmented nipple. The other nipple of each animal was treated with vehicle only and served as a control. Chromameter measurement after seven weeks of treatment revealed a dose-dependent lightening effect of +9.6 L* and nearly 18 L* units respectively. No visible signs of irritation were observed at that time.

Four groups of three guinea pigs each were treated respectively with Compound I, SFLLRN, FSLLRN and SLIGRL at 10 $\mu$M, twice daily five days per week for eight weeks. Chromameter measurement after six weeks demonstrates a lightening effect by Compound I and a darkening effect by SLIGRL, the PAR-2 agonist. The results of this example are set forth in FIG. 7.

EXAMPLE 8

Thrombin and Trypsin Inhibitors and PAR-2 Agonists Affect Pigmentation In vivo

A Yucatan microswine was treated with Compound I, SFLLRN, FSLLRN and SLIGRL at 10 $\mu$M. Each compound was applied to two sites on the pig twice daily, five days per week for eight weeks. After eight weeks of treatment, chromameter measurements were taken. The application of Compound I resulted in a visible lightening effect. The PAR-2 agonist SLIGRL resulted in a darkening effect as measured by chromameter. SFLLRN and FSLLRN had no significant effects.

Figure 8:
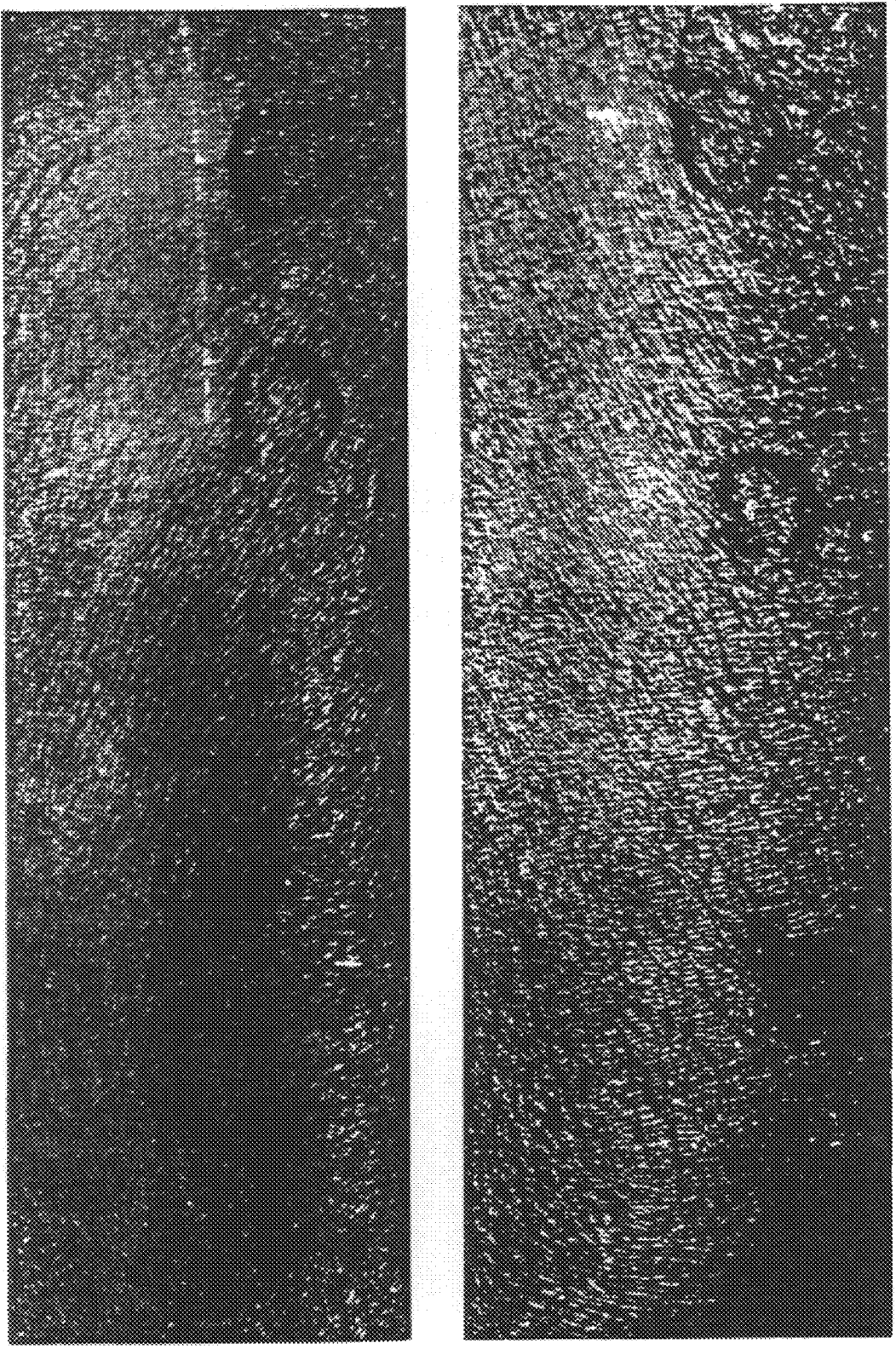
FIG. 8 is a photograph of Yucatan Swine skin which has been treated with compositions of this invention for depigmentation of skin.
Figure 9:
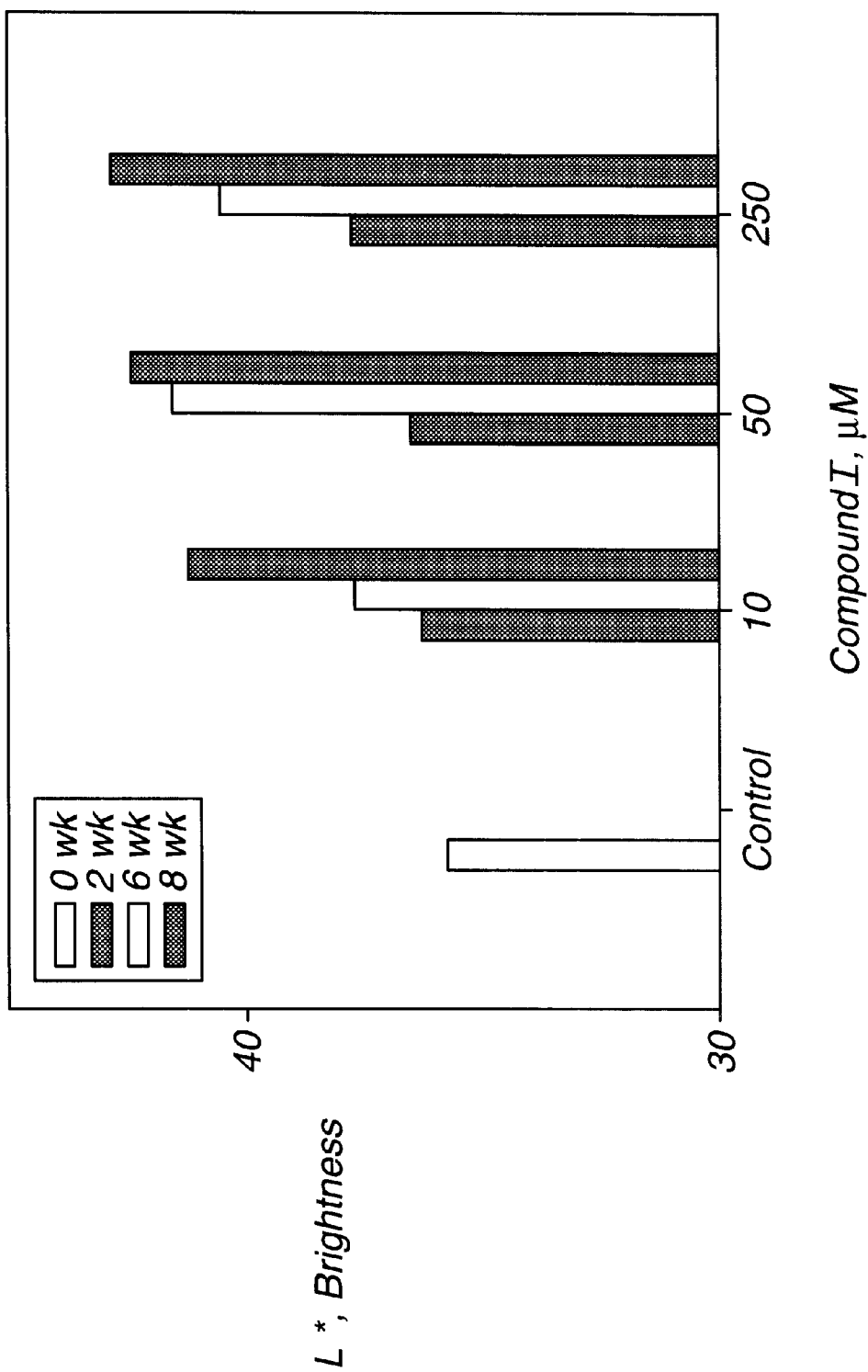
FIG. 9 is a graph depicting the brightness of Yucatan Swine skin during the course of treatment in accordance with the methods and compositions of this invention.
Figure 10A:
FIGS. 10A, 10B, 10C and 10D are photographs of F&M stained histological sections of Yucatan Swine skin treated with compositions containing Compound I in accordance with methods of this invention at concentrations of 0, 10 µM, 50 µM and 250 µM respectively.
Figure 10B:
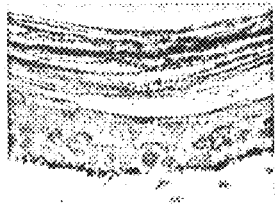
Figure 10C:
Figure 10D:

Two Yucatan swine were treated for seven and a half weeks, or for ten weeks, twice daily, five days per week, with increasing concentrations of Compound I. Four concentrations of active compound were used, as follows: 0, 10, 50 and 250 $\mu$M. Two sites per concentration were placed on opposite sides of the swine dorsum. Chromameter measurements were taken before treatment started and every two weeks thereafter. Pictures were taken periodically and at the end of the experiment. A visible lightening effect was observed during the 4th, 5th and 6th weeks of treatment, for the 250, 50 and 10 µM treatments, respectively. By the eighth week, the whitening effect of the two highest doses was similar. These results are illustrated in FIG. 8. The chromameter readings (L*, measuring brightness) during the treatment course of one swine are shown in FIG. 9. A saturation effect is observed, which is a time and concentration dependent. This example demonstrates a visual depigmenting effect by Compound I, in the animal model system most resemble pigmented human skin.

At the end of these experiments, biopsies were taken for histological and electron microscopy (EM) analyses. Histological samples were stained with H&E and F&M. H&E staining showed that there was no irritation, inflammatory response or changes in skin architecture, demonstrating the safety of using Compound I over long periods of time. F&M staining demonstrated that there was reduced pigmentation in the treated samples, both in the basal layer and throughout the epidermis. These results are illustrated in FIG. 10. Untreated and vehicle-treated samples (FIG. 10A) were identical and darkest. The 10 µM treatment (FIG. 10B) showed reduced pigmentation and the 50 and 250 µM treatments (FIGS. 10C, 10D, respectively) were the lightest.

The results of this example suggest that the maximal whitening effect of Compound I could be achieved with higher concentration over a shorter period of time or with lower concentration over a longer period of time. Thus, at least two difference regimens may be used to achieve the desired skin whitening results.

EXAMPLE 9

Figure 11C:

Ultrastructural Studies Demonstrate the Effect of Compound I On the Skin In Vitro and In Vivo Ultrastructural analysis was performed on MelanoDerm equivalents and swine skin sites treated with Compound I. MelanoDerm equivalents treated with Compound I were analyzed for melanosome formation and distribution using electron microscopy. Treated samples contained more melanosomes, but less mature melanosomes, i.e., melanosomes which evidence reduced melanin production, within the melanocytes, relative to untreated controls (FIGS. 11A, 11B). Dendrites containing melanosomes were easily identified within treated keratinocytes (FIG. 11C), but were difficult to find within control keratinocytes. This suggests abnormal melanosome formation and slow or impaired melanosome transfer into keratinocytes in the treated samples.

Figure 11D:
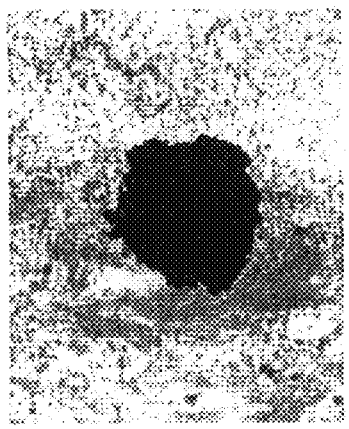
FIGS. 11D and 11G are photographs of electron micrographic views of untreated sites of Yucatan Swine skin.
Figure 11E:
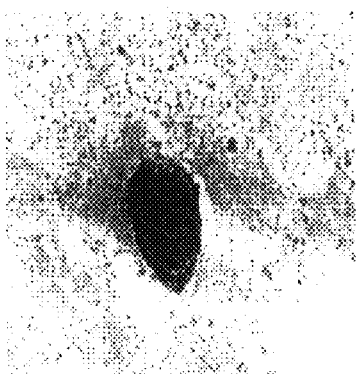
FIGS. 11E, 11F and 11H are photographs of electron micrographic views of Yucatan Swine skin treated with compositions of this invention.
Figure 11F:
Figure 11G:
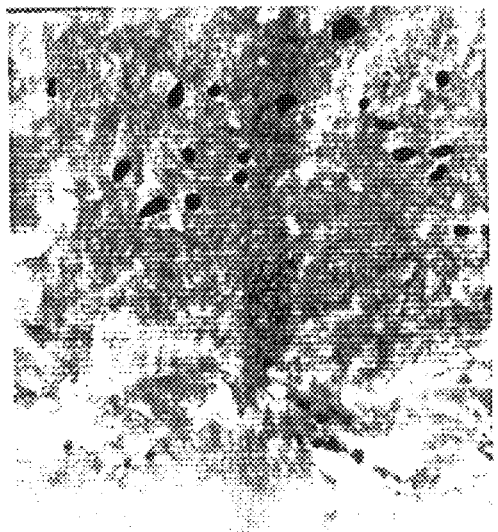
Figure 11H:
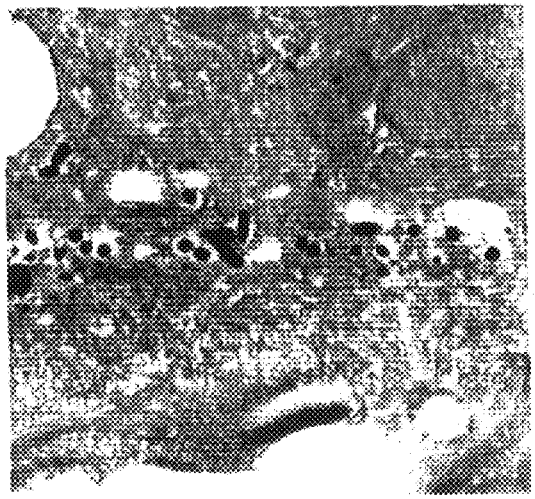

Skin samples from Yucatan swine treated with compound I for eight weeks, as described in example 8, were also analyzed by electron microscopy. Melanosomes within keratinocytes of treated sites were smaller and less pigmented, compared to controls (FIGS. 11D, 11E and 11F). Moreover, the distribution of melanosomes within the treated skins was abnormal. Melanosomes were detected mainly at the epidermal-dermal border, compared to a random distribution in untreated controls (FIGS. 11G, 11H). While we cannot rule out other mechanisms, we suggest that Compound I treated keratinocytes were unable to actively take or receive melanosomes from the presenting dendrites.

EXAMPLE 10

The in vivo depigmenting effect of Compound I is reversible

Figure 12A:
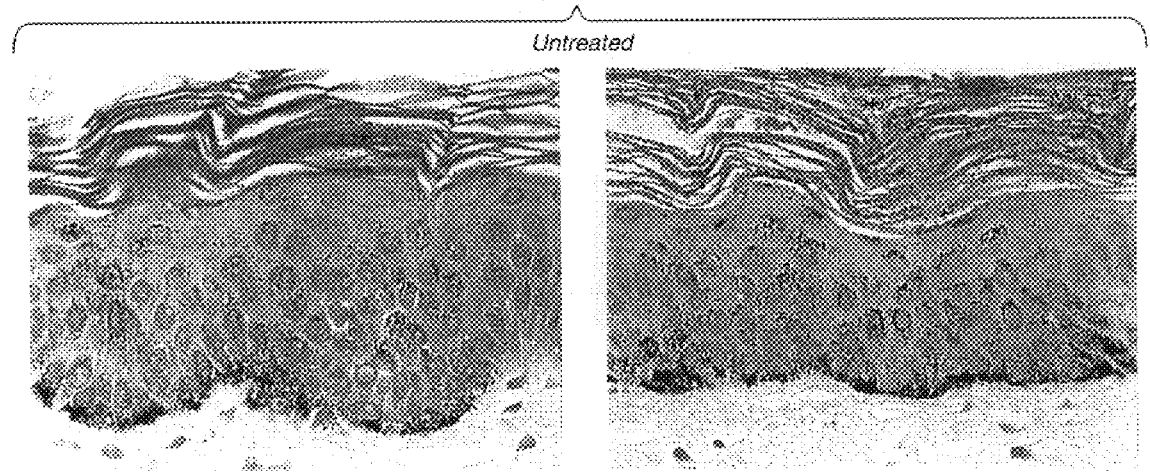
FIGS. 12A, 12B, 12C, 12D and 12E are photographs of histological F&M stained sections of Yucatan Swine skin, as follows: 12A shows untreated skin; 12B shows skin treated with compositions of this invention after eight weeks of treatment; 12C shows skin one week after stopping treatment; 12D shows skin two weeks after stopping treatment and 12E shows skin four weeks after stopping treatment.
Figure 12B:
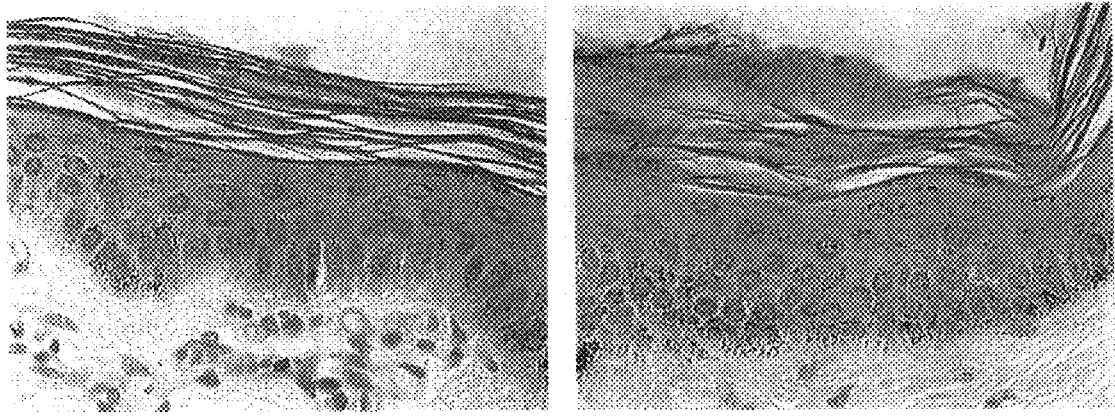
Figure 12C:
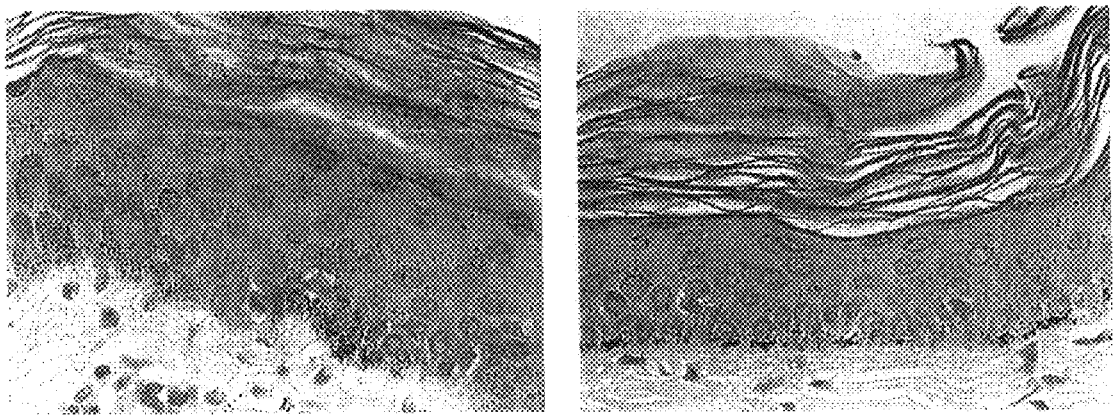
Figure 12D:
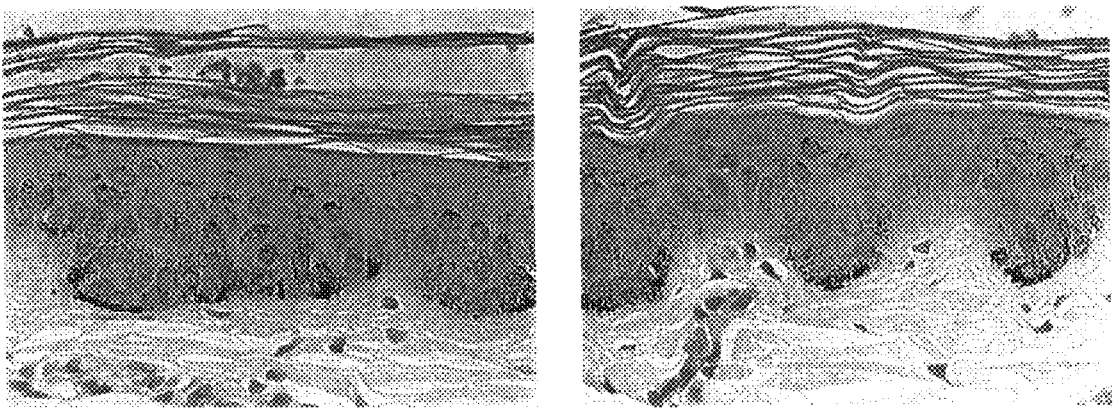
Figure 12E:
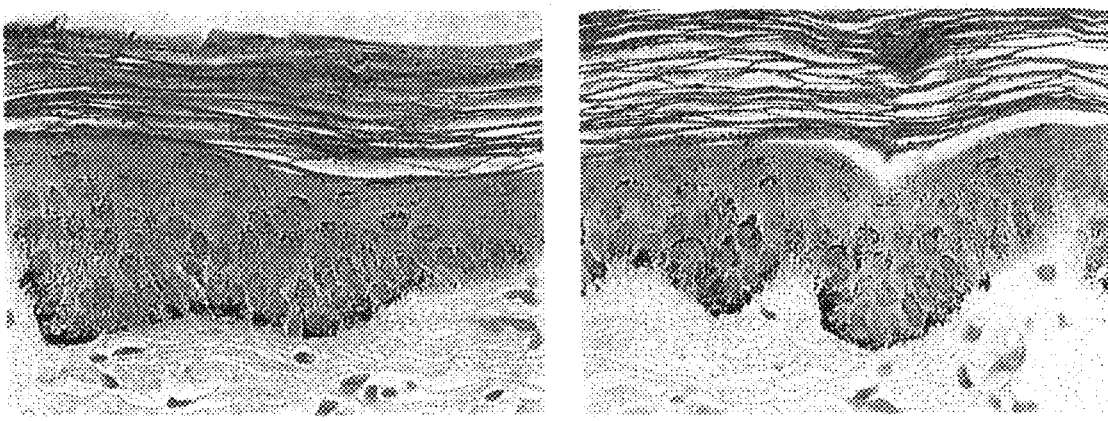

A Yucatan swine was treated with Compound I, 250 µM, for eight weeks, twice daily, five days a week, on eight sites. All sites showed visible depigmentation by the end of the treatment period, as set forth in FIG. 12B. For the following four weeks (starting at week nine of the experiment), the color of the treated sites was monitored, and two biopsies were taken each week from two treated sites. Untreated sites were biopsied as well. The depigmenting effect could be visualized at one and two weeks post treatment, and a complete reversal was observed by the forth week. Histological examination of F&M stained skin sections confirmed the repigmentation observed visually (as indicated in FIG. 12). As early as one week post treatment, repigmentation was demonstrated histologically. The visual observations correlate with the histological demonstration of stratum corneum pigmentation. This example demonstrates that Compound I does not induce a permanent damage to the pigmentation machinery, and its effect is reversible in vivo. FIG. 12A shows two histological F&M stained sections of sites which were not treated with Compound I. FIG. 12B shows two histological F&M stained sections of sites which were treated with Compound I for eight weeks. FIG. 12C shows sections of sites which were treated for eight weeks with Compound I, one week after treatment was stopped. FIG. 12D shows sections of sites which were treated for eight weeks with Compound I, two weeks after treatment was stopped. FIG. 12E shows sections of sites which were treated for eight weeks with Compound I, four weeks after treatment was stopped. As indicated in FIG. 12E, the sections were fully repigmented four weeks after the end of treatment.

EXAMPLE 11

Preparation of naturally-derived products containing STI

Example 1 demonstrates that the presence of soybean trypsin inhibitor in any lightening formulation is desirable for its depigmenting activity. Based on analytical testing, it has been determined that soybean milk and soybean paste are rich sources of soybean trypsin inhibitor.

To make soybean paste, soybeans were first soaked in deionized or purified water for several hours. The soybeans were ground after they were fully hydrated, with the addition of small quantities of water, if needed, to smoothen the paste. To make soybean milk, the same procedure was performed with the addition of more water. (The grinding process allows the soybean milk to be extracted). After collection, the soybean milk was filtered to remove any residual parts of the bean husk.

Soybean milk, soybean paste and miso were prepared to be used as naturally-derived materials that contain STI and are able to lighten skin color.

EXAMPLE 12

Figure 13:
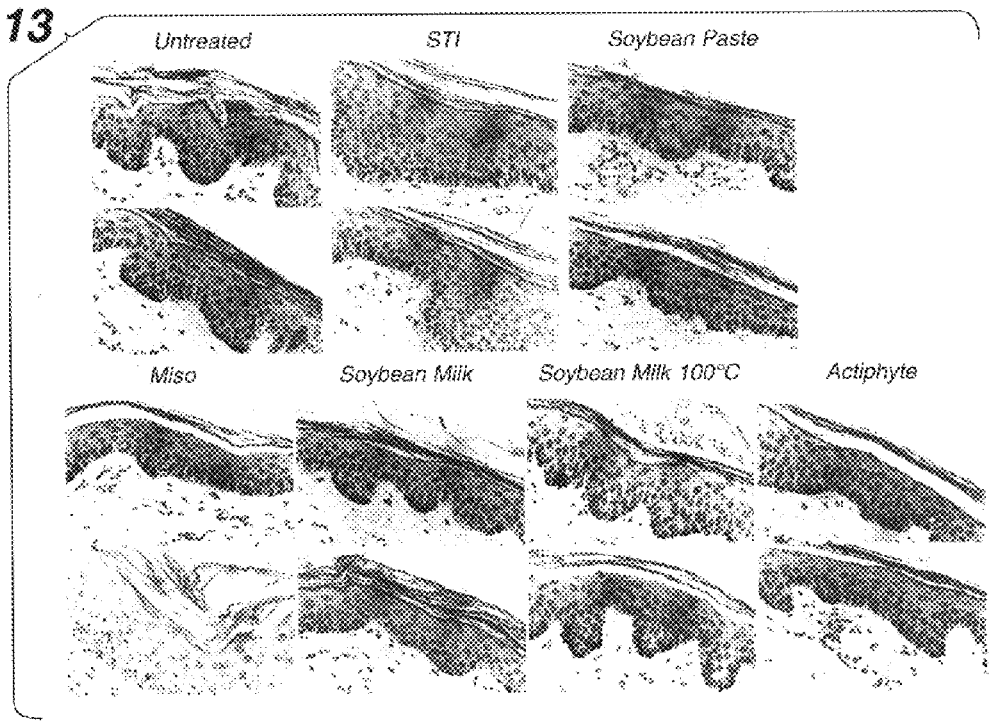
FIG. 13 is a photograph of F&M stained histological sections taken from Yucatan Swine skin treated with compositions of this invention.

Treatment With Naturally-Derived Materials that affect the PAR-2 Pathway Induces Depigmentation Two Yucatan swine were treated for eight and ten weeks, twice a day, five days a week, with different soybean- and lima-bean-derived products. These natural products include soybean paste, soybean protein acid hydrolysate, miso, native and boiled soybean milk, and a commercially available extract of soybean (Actiphyte™ of Active Organics, Dallas Tex.), as well as purified STI, and different preparations of trypsin inhibitors from soybeans and limabeans. At seven weeks of treatment, all sites were visually lighter than the surrounding skin, except for the boiled soybean milk and the soybean protein acid hydrolysate treated sites. Histological analysis of biopsies from the treated sites following F&M staining confirmed the depigmenting effect of the soybean and limabean products. An example of such histological data is given in FIG. 13. The lack of depigmenting activity in the boiled soybean milk and in the soy protein acid hydrolysate is explained by the denaturation or the degradation of the soy proteins in these preparations, respectively. We theorize that the active depigmenting agents in the soybean and limabean products are soybean trypsin inhibitor (STI) and limabean trypsin inhibitor, respectively. (Example 1 shows the depigmenting effect of STI in vitro). This example demonstrate that natural extracts containing trypsin inhibitory activity could be used as whitening agents which affect the PAR-2 pathway.

EXAMPLE 13

An STI in liposome formulation can lighten human age spots

An individual with three age spots on the dorsum of their hand was treated for eight weeks, twice a day, with the following: The age spot located closest to the arm was treated with placebo, containing 20 mg/ml of liposomes. The middle age spot was not treated. The third age spot was treated with STI, 1%, in liposomes (20 mg/ml).

GDL liposomes were prepared as set forth in Niemiec, et al., above, with the exception of the following changes: the non-ionic liposomal formulation contained glycerol dilaurate (Emulsynt GDL, ISP Van Dyk)/cholesterol (Croda)/ polyoxyethylene-10-stearyl ether (Brij76, ICl)/ polyoxyethylene-9-lauryl ether, as at ratio of 37.5:12.5:33.3:16.7. Hepes buffer, 0.05M, pH 7.4 (Gibco-BRL of Gaithersburg, Md.) was used as the aqueous phase in the preparation of the liposomes. UV and visible light digital pictures were taken at time 0, 4 and 8 weeks of treatment. L* (brightness) values were calculated from the images using Adobe Photoshop.

Figure 14:
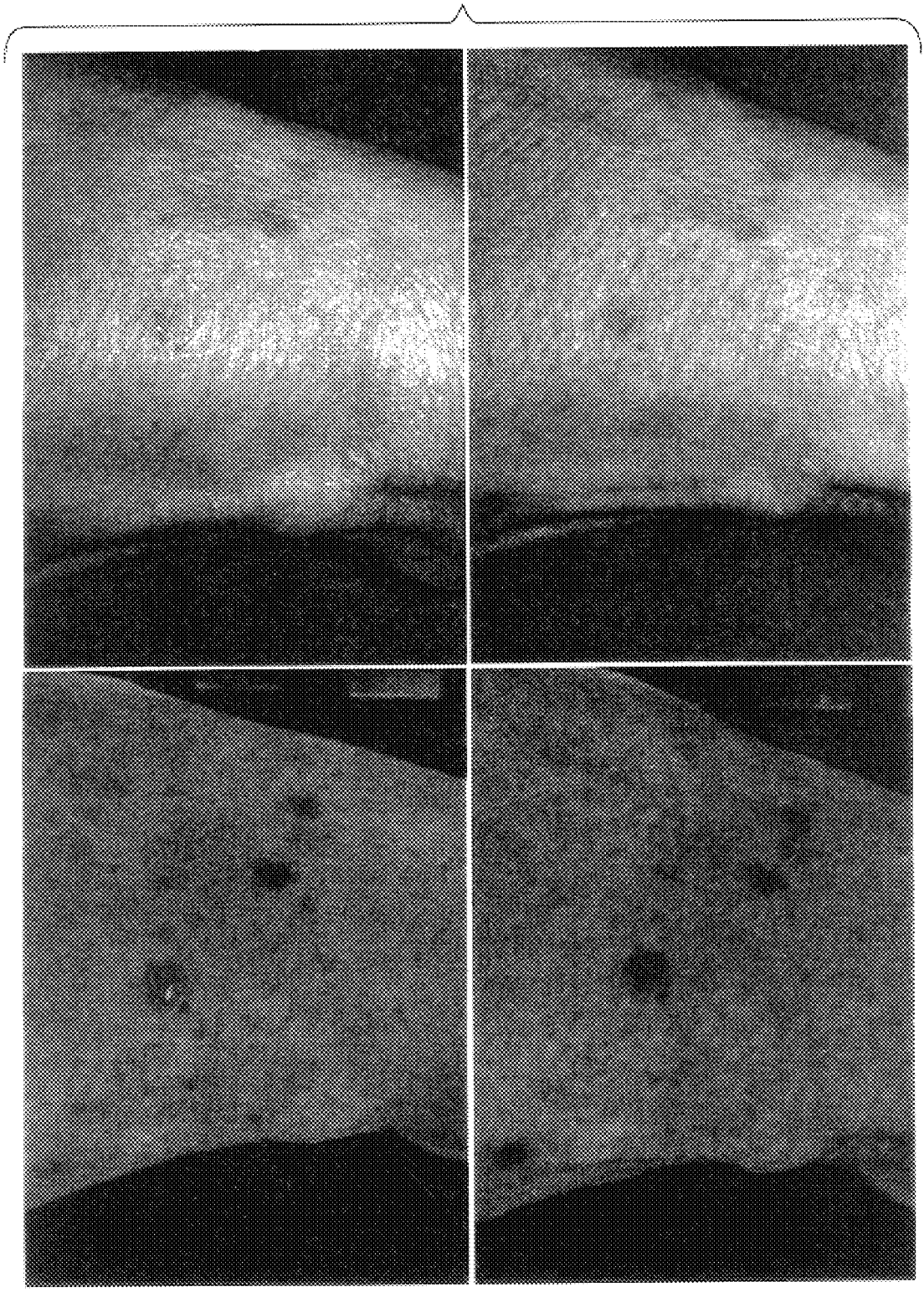
FIG. 14 contains ultraviolet and visible light digital photographs of human skin prior to treatment and subsequent to treatment with compositions of this invention.

As shown in FIG. 14, the age spot treated with STI became lighter following 8 weeks of treatment. FIG. 14 is a composite of four pictures. The left panel is the visible light pictures of the hand, before (upper) and after (lower) 8 weeks of treatment. At this orientation the top age spot is the placebo-treated, the middle age spot is untreated, and the lower age spot is the STI-treated. The right panel shows the same hand at the same time points, using UV-photography. UV light enables the visualization of pigment deeper in the skin, demonstrating that the STI whitening effect was not superficial. FIG. 14 clearly demonstrates that the STI formulation was able to lighten the lower age-spot. An increase of 15 L* units was calculated for this STI-treated site, further demonstrating the ability of this treatment to lighten age spots.

EXAMPLE 14

Depigmenting formulations with soybean milk

In making the soybean milk, it was discovered that the rich emolliency of the milk would be desirable in a skin care formulation. Because water is used as the predominant ingredient of any oil-in-water emulsion, and in many other skin-care formulations we hypothesized that the soymilk could be used to substitute for the deionized water in such formulations. However, we expected that this type of formulation would not be physically stable due to the immiscibility of the oil and water components of the soybean milk. Surprisingly, we found that this substitution of soybean milk for water was physically stable. Formulations utilizing soybean milk should contain between about 1% and about 99% of soybean milk, more preferably from about 80% to about 95% soybean milk. Preferably, this and similar formulations should include a viscosity builder in an amount from about 0% to about 5% (more preferably, from about 0.1 to about 2%), one or more emollients in an amount up to about 20% and/or emulsifiers in an amount from about 0.1% to about 10% (more preferably from about 3 to about 5%), and, optionally, a spreading agent in an amount from about 0 to about 5% (more preferably from about 1 to about 2%), a preservative, a chelating agent or a humectant. The preservative should be present in an effective amount in order to preserve integrity of the milk and maintain the composition's activity. Sufficient thickener should be present to impart body to the formulation without causing it to become so viscous that it would hinder spreadability, e.g., from about 0 to about 10%, more preferably from about 3 to about 5%. Sunscreen, antioxidants, vitamins other depigmenting agents and other skin care topical ingredients may also be incorporated into the compositions of this invention.

A particularly preferred example of a depigmenting formulation substituting soymilk for water is shown in Table E below.

TABLE E

| Ingredient | Function | % Wgt/Wgt |
|---|---|---|
| soybean milk | Vehicle, depigmenting | 84.9% |
| aluminum starch octenyl succinate | viscosity builder | 0.75% |
| cyclomethicone | spreading agent | 2% |
| PEG 6-capric/caprylic triglycerides | emollient/emulsifier | 3% |
| phenoxyethanol | preservative | 0.75% |
| sucrose cocoate | emollient/emulsifier | 1% |
| Na$_2$EDTA | chelating agent | 0.1% |
| glycerin | humectant | 2.5% |
| polyacrylamide; isoparaffin; laureth-7 | thickener | 5% |

STI, soybean paste and other trypsin inhibitor-containing natural extracts can be incorporated into such formulations to provide increasing concentrations of the serine protease inhibitor. Use levels of the added active ingredient can range between 0.01% to 15% in a formulation. Other depigmenting agents, including PAR-2 inhibitors, tyrosinase inhibitors, hydroquinones, soy products, ascorbic acid and its derivatives, as well as other ingredients with skin care benefits could also be incorporated into this formulation.

EXAMPLE 15

An Oil-in-water Emulsion depigmenting formulation

Two examples of a depigmenting formulation with oil-in-water emulsion are presented in Table F. A formulation with STI, where STI could be replaced with any naturally-derived serine protease inhibitor, or with any naturally-derived extract or fraction thereof containing serine protease inhibitors, is described in column 4 of Table F. A similar formulation with Compound I is presented in column 5 of Table F. Compound I in this composition could be replaced with similar compounds, or with serine protease inhibitors or with any PAR-2 inhibitor materials having high therapeutic indices, whether derived synthetically or naturally, as the active ingredient. Suggested ranges for the ingredients in such formulations are also listed in Table F. The deionized water content of these formulations could be replaced with soybean milk.

TABLE F

| Phase | CTFA Name | Function | % W/W | % W/W | Ranges |
|---|---|---|---|---|---|
| OIL | Cetearyl Glucoside | Surfactant | 1.4 | 1.4 | 0.1–2.8 |
| | C12–15 Alkyl Benzoate | Surfactant | 4.0 | 4.0 | 1–6 |
| | Octyl Hydroxystearate | Emollient | 1.0 | 1.0 | 0–5 |
| | Dimethicone | Spreading Agent | 1.0 | 1.0 | 0–5 |
| | Cyclomethicone | Spreading Agent | 1.0 | 1.0 | 0–5 |
| | Cetyl Alcohol | Emollient | 2.5 | 2.5 | 0–4 |
| | Butylated Hydroxytoluene | Anti-oxidant | 0.1 | 0.1 | 0–0.5 |
| | Octyl Methoxycinnamate | Sunscreen | 6.0 | 6.0 | 0–10 |
| | Propylparaben | Preservative | 0.5 | 0.1 | 0–0.5 |
| | Vitamin E acetate | Anti-oxidant | 0.5 | 0.5 | 0–0.5 |
| | Tocopherol Acetate | Anti-oxidant | 0.5 | 0.5 | 0–0.5 |
| AQUE-OUS | Glycerine | Humectant | 3.0 | 3.0 | 0–20 |
| | D-Pathenol | Pro-Vitamin | 0.5 | 0.5 | 0–5 |
| | Disodium EDTA | Chelator, whitening agent | 0.1 | 0.1 | 0.01–1 |
| | Methyl Paraben | Preservative | 0.2 | 0.2 | 0–0.3 |
| | Carbomer | Thickener | 0.35 | 0.35 | 0–3 |
| | Deionized Water or Soybean Milk | Carrier I Whitening Agent | 76.35 | 77.5 | 50–80 |
| | STI or natural extract | Whitening Agent | 1.0 | 0 | 0–15 |
| | Compound I | Whitening Agent | 0 | 0.25 | 0–1 |

To prepare this formulation, the ingredients of the lipid phase were combined and mixed at 85° C., and then cooled to 60° C. In a separate vessel, the carbopol was slowly added to the water or to the soybean milk. After mixing for ten minutes the rest of the aqueous phase ingredients were added and the mix was heated to 60° C. The two phases were then combined, mixed for ten minutes, and cooled to room temperature. Of course, one or more depigmentation agents may be combined within the same formulation, in this Example and in the following examples and other embodiments of the methods and compositions of this invention.

EXAMPLE 16

Depigmenting Composition (Oil-in-Water Emulsion)

Two additional examples of an oil-in-water emulsion depigmenting formulation are presented in Table G. A formulation with STI, where STI could be replaced with any naturally-derived serine protease inhibitor, or with any naturally-derived extract or fraction thereof containing serine protease inhibitors, is described in column 3 of Table G. A similar formulation with Compound I is presented in column 4 of Table G. Compound I in this composition could be replaced with similar compounds or with serine protease inhibitor or with any PAR-2 inhibitor materials having high therapeutic indices, whether derived synthetically or naturally, as the active ingredient. Suggested ranges for the ingredients in such formulations are also listed in Table G. The deionized water content of these formulations could be replaced with soybean milk.

TABLE G

| CTFA Name | Function | % W/W | % W/W | Pref'd. Ranges |
|---|---|---|---|---|
| Ethanol | Solvent | 12.0 | 12.0 | 5–20 |
| Propylene Glycol | Solvent | 3.0 | 3.0 | 1–10 |
| Hydroxyethylcellulose | Thickener/Polymer | 0.2 | 0.2 | 0–3 |
| Acrylates/C10–30 Alkyl Acrylate Crosspolymer | Thickener/Polymer | 1.0 | 1.0 | 0–3 |
| Panthenol (98%) | Pro-Vitamin/Humectant | 1.5 | 1.5 | 0.1–3 |
| Fragrance | Fragrance | 0.5 | 0.5 | 0–0.5 |
| Isohexadecane | Spreading Agent | 4.0 | 4.0 | 0–5 |
| Vitamin E acetate | Anti-oxidant | 1.0 | 1.0 | 0–2 |
| Sodium Hydroxide | Neutralizer | 0.35 | 0.35 | 0.1–0.5 |
| Glycerine | Humectant | 3.0 | 3.0 | 0–20 |
| Deionized Water or Soybean Milk | Carrier/Whitening Agent | 72.2 | 71.95 | 60–80 |
| Compound I | Whitening Agent | 0 | 0.25 | 0–1 |
| STI or natural extract | Whitening/Agent | 1.0 | 0 | 0–15 |

To prepare this formulation, the hydroxyethylcellulose was slowly added to the water or to the soybean milk and stir until completely dissolved. In a separate container the Acrylates/C10–30 Alkyl Acrylate Crosspolymer was added and stir until completely dissolved. The content of the two containers was combined and mixed for 20 minutes. Vitamin E acetate was then added and mixed, following by the addition of Isohexadecane and Panthenol (98%). After mixing for five minutes the STI, or the natural extract, or Compound I were added together with Propylene Glycol, and stirred for 5 minutes. Next, glycerine was added and the formulation was stirred for 20 minutes. Finally, the pH was adjusted with sodium hydroxide to 8 for STI (range is 6–8.5) or to 7 for Compound I (range is 5.5–8.5).

EXAMPLE 17

Depigmenting Composition (Water-In-Oil Emulsion)

An example of a depigmenting formulation with water-in-oil emulsion is presented in Table H. A formulation with STI, where STI could be replaced with any naturally-derived serine protease inhibitor, or with any naturally-derived extract or fraction thereof containing serine protease inhibitors, is described in column 4 of Table H. A similar formulation with Compound I is presented in column 5 of Table H. Compound I in this composition could be replaced with similar compounds or with serine protease inhibitor or with any PAR-2 inhibitor materials having high therapeutic indices, whether derived synthetically or naturally, as the active ingredient. Suggested ranges for the ingredients in such formulations are also listed in Table H. The deionized water content of these formulations could be replaced with soybean milk.

TABLE H

| Phase | CTFA Name | Function | % W/W | % W/W | Pref'd Ranges |
|---|---|---|---|---|---|
| OIL | Mineral Oil | Emollient | 25.0 | 25.0 | 40–80 |
| | Sorbitan Monooleate | Surfactant | 5.0 | 5.0 | 1–6 |

TABLE H-continued

| Phase | CTFA Name | Function | % W/W | % W/W | Pref'd Ranges |
|---|---|---|---|---|---|
| | Stearyl Alcohol | Emollient | 25.0 | 25.0 | 20–60 |
| | Dimethicone | Spreading Agent | 1.0 | 1.0 | 1–5 |
| | Cetyl Alcohol | Emollient | 2.0 | 2.0 | 0.1–10 |
| | Hydrogenated Lecithin | Anti-oxidant | 3.0 | 3.0 | 0–10 |
| | Parsol MCX | Sunscreen | 3.0 | 3.0 | 0–10 |
| | Propylparaben | Preservative | 0.5 | 0.5 | 0.01–0.5 |
| | Vitamin E acetate | Anti-oxidant | 0.5 | 0.5 | 0.01–0.5 |
| AQUEOUS | Glycerine | Humectant | 3.0 | 3.0 | 0–20 |
| | Methyl Paraben | Preservative | 0.2 | 0.2 | 0.01–0.3 |
| | Water or Soy Milk | Carrier I Whitening Agent | 30.8 | 31.55 | 20–45 |
| | STI | Whitening Agent | 1.0 | 0 | 0–10 |
| | Cpd I | Whitening Agent | 0 | 0.25 | 0–1 |

To prepare this formulation the stearyl alcohol and mineral oil were melted at 70° C. The other oil phase ingredients were added and the mixture heated to 75° C. The aqueous phase ingredients, which have been previously dissolved in the bulk phase water or Soy Milk and warmed to 70° C., were then added and the mixture was stirred until it congealed.

EXAMPLE 18

Depigmentation Composition (Aqueous Gel)

Two examples of a depigmenting formulation with aqueous gel are presented in Table J. A formulation with STI, where STI could be replaced with any naturally-derived serine protease inhibitor, or with any naturally-derived extract or fraction thereof containing serine protease inhibitors, is described in column 3 of Table J. A similar formulation with Compound I is presented in column 4 of Table J. Compound I in this composition could be replaced with similar compounds or with serine protease inhibitor or with any PAR-2 inhibitor materials having high therapeutic indices, whether derived synthetically or naturally, as the active ingredient. Suggested ranges for the ingredients in such formulations are also listed in Table J. The deionized water content of these formulations could be replaced with soybean milk.

TABLE J

| CTFA Name | Function | % W/W | % W/W | Pref'd Ranges |
|---|---|---|---|---|
| Octoxynol-13 | Surfactant | 0.2 | 0.2 | 0.05–0.5 |
| 2,4-Hexadienoic Acid | Preservative | 0.1 | 0.1 | 0–0.3 |
| Benzenemethanol | Preservative | 1.0 | 1.0 | 0–2 |
| Disodium EDTA | Chelator/Preservative | 0.05 | 0.05 | 0.01–0.2 |
| Ascorbic Acid | Anti-oxidant | 0.1 | 0.1 | 0–0.2 |
| Sodium Metabisulfite | Anti-oxidant | 0.2 | 0.2 | 0–0.3 |
| Carbomer | Thickener | 1.5 | 1.5 | 0–3.0 |
| NaOH % 20 Soln. | Neutralizer | 2.45 | 2.45 | 0.1–5 |
| DEIONIZED Water or Soybean Milk | Carrier/Whitening Agent | 93.4 | 94.15 | 85–98 |
| STI or natural extract | Whitening Agent | 1.0 | 0 | 0–15 |
| Compound I | Whitening Agent | 0 | 0.25 | 0–1 |

To prepare this formulation, the Disodium EDTA, sodium metabisulfite and ascorbic acid were slowly added to the water or to the soybean milk and stir until completely dissolved. STI, natural extracts or Compound I were then added and mixed slowly for five minutes. The speed of agitation was then increased and carbopol was added. The composition was mixed for 30 minutes or until the dispersion was free of "fish eyes", which are non-dispersed clear lumps, and heated to 50° C. In a separate container, the slurry phase was prepared by combining Octoxynol-13, 2,4-Hexadienoic acid, and Benzenemethanol and stirring ten minutes at 40–50° C. The slurry was then added slowly to the aqueous phase, mixed, and cooled to 45° C. 20% sodium hydroxide solution was used to pH the composition to pH of 7.0 (range is 5.5–8.5). This was mixed to homogeneity using agitation or sweep vessel.

EXAMPLE 19

Solvent-based Depigmenting Composition

An example of a depigmenting formulation containing solvent is presented in Table K. A formulation with STI, where STI could be replaced with any naturally-derived serine protease inhibitor, or with any naturally-derived extract or fraction thereof containing serine protease inhibitors, is described in column 3 of Table K. A similar formulation with Compound I is presented in column 4 of Table K. Compound I in this composition could be replaced with similar compounds or with serine protease inhibitor or with any PAR-2 inhibitor materials having high therapeutic indices, whether derived synthetically or naturally, as the active ingredient. Suggested ranges for the ingredients in such formulations are also listed in Table K. The deionized water content of these formulations could be replaced with soybean milk.

TABLE K

| CTFA Name | Function | % W/W | % W/W | Range |
|---|---|---|---|---|
| Ethanol | Solvent (1) | 70 | | 40–90 |
| Propylene Glycol | Solvent (2) | 29 | | 1–40 |
| Deionized Water | Carrier | q.s. | | 1–40 |
| STI | Whitening Agent | 0 | | |
| Compound I | Whitening Agent | 1 µM | | .00001–1 |

To prepare this formulation Compound I was dissolved in water. The ethanol and propylene glycol were mixed and combined with the aqueous solution containing Compound I.

In summary, we have demonstrated that activation of the keratinocyte receptor PAR-2 results in increased pigmentation. Preferably, such activation may be accomplished by the use of trypsin or SLIGRL or SLIGKVD or other SLIGRL or SLIGKVD derivatives. We have also demonstrated that whitening may be accomplished by the use of serine protease inhibitors or PAR-2 antagonists, as well as by melanosome-transfer blockers. Other compounds known to those of skill in the art that inhibit melanosome transfer into keratinocytes could also be used as depigmenting agents.

Compound I, a trypsin and thrombin inhibitor, for example, inhibits melanosome transfer to keratinocytes. STI works by the same mechanism. The accumulation of undelivered melanosomes in the melanocytes could induce a negative feed back mechanism, that slows new melanosome formation. The production of TRP-1, the major glycoprotein in melanocytes, is down-regulated, which leads to destabilization of tyrosinase. This results in reduced melanin formation, and in a color switch to a lighter brown, as the ratio of TRP-1:TRP-2 is reduced. The melanosomes accumulation in the melanocyte after Compound I treatment, or after STI treatment, therefore, have reduced and altered melanin content, which adds to the whitening effect of compound I or STI.

Phagocytosis and PAR-2 mediated ICAM-1 Expression

This invention is based on the discovery that PAR-2-mediated phagocytosis and PAR-2 mediated ICAM-1 expression can be specifically altered. This ability to specifically increase and decrease these cellular functions permits the treatment and prevention of disorders, which would be ameliorated by an increase, or decrease of phagocytosis and/or ICAM-1 expression. Accordingly, this invention provides various compositions and methods for the treatment of disorders ameliorated by the specific alteration of phagocytosis and/or ICAM-1 expression.

More specifically, this invention provides a number of compositions of matter for treating and preventing certain mammalian disorders. These compositions include the following:

(1) a composition of matter for treating a mammal afflicted with a disorder ameliorated by an increase in phagocytosis or ICAM-1 expression in appropriate cells, which comprises (a) a therapeutically effective amount of an agent that increases phagocytosis or ICAM-1 expression, and (b) a pharmaceutically or cosmetically acceptable carrier;

(2) a composition of matter for treating a mammal afflicted with a disorder ameliorated by a decrease in phagocytosis or ICAM-1 expression in appropriate cells, which comprises (a) a therapeutically effective amount of an agent that specifically decreases phagocytosis or ICAM-1 expression, and (b) a pharmaceutically or cosmetically acceptable carrier;

(3) a composition of matter for preventing in a mammal a disorder ameliorated by an increase in phagocytosis or ICAM-1 expression in appropriate cells, which comprises (a) a prophylactically effective amount of an agent that specifically increases phagocytosis or ICAM-1 expression, and (b) a pharmaceutically or cosmetically acceptable carrier; and (4) a composition of matter for preventing in a mammal a disorder ameliorated by a decrease in phagocytosis or ICAM-1 expression in appropriate cells, which comprises (a) a prophylactically effective amount of an agent that specifically decreases phagocytosis or ICAM-1 expression, and (b) a pharmaceutically or cosmetically acceptable carrier.

This invention also provides methods of altering the phagocytosis or ICAM-1 expression level in a cell. The invention first provides a method of increasing phagocytosis or ICAM-1 expression in a mammalian cell, comprising contacting the cell with an effective amount of an agent that specifically increases phagocytosis or ICAM-1 expression. Second, this invention provides a method of decreasing phagocytosis or ICAM-1 expression in a mammalian cell, comprising contacting the cell with an effective amount of an agent that specifically decreases phagocytosis or ICAM-1 expression.

This invention further provides methods of treatment and prophylaxis regarding disorders affected by the alteration of phagocytosis or ICAM-1 expression. Specifically, this invention provides the following:

(1) a method of treating a mammal afflicted with a disorder ameliorated by an increase in phagocytosis or ICAM-1 expression in appropriate cells, which comprises administering to the mammal a therapeutically effective amount of an agent that specifically increases phagocytosis or ICAM-1 expression;

(2) a method of treating a mammal afflicted with a disorder ameliorated by a decrease in phagocytosis or ICAM-1 expression in appropriate cells, which comprises administering to the mammal a therapeutically effective amount of an agent that specifically decreases phagocytosis or ICAM-1 expression;

(3) a method of preventing in a mammal a disorder ameliorated by an increase in phagocytosis or ICAM-1 expression in appropriate cells, which comprises administering to the mammal a prophylactically effective amount of an agent that specifically increases phagocytosis or ICAM-1 expression; and (4) a method of preventing in a mammal a disorder ameliorated by a decrease in phagocytosis or ICAM-1 expression in appropriate cells, which comprises administering to the mammal a prophylactically effective amount of an agent that specifically decreases phagocytosis or ICAM-1 expression.

The instant composition of matter can be of any form known in the art. In one embodiment, the composition comprises a pharmaceutically acceptable carrier and one or more discrete pharmaceutical compounds that function as the agent that specifically alters phagocytosis or ICAM-1 expression. In another embodiment, the composition of matter comprises a naturally-occurring composition, or an extract or component thereof, which is deemed pharmaceutically or cosmetically acceptable. Such naturally occurring compositions contain certain components which function as active agents, and numerous others that serve as pharmaceutical or cosmetically carriers. The instant compositions can be artificial, naturally occurring, or a combination thereof. In addition, the compositions can be of any physical form known in the art, such as liquids (e.g., solutions, creams, lotions, gels, injectables), solids (e.g., tablets, capsules, powders, granules), aerosols, and coatings.

Natural compounds that inhibit trypsin, such as serine protease inhibitors, and in particular, soybean trypsin inhibitor ("STI"), can be used for this invention. Soybean extracts, limabean extracts and similar extracts, and other natural products made from soybean and the like, such as soybean milk, soybean paste, miso, trypsin inhibitor from soybean or limabean and the like, can also reduce phagocytosis by this mechanism. In the preferred embodiment, the naturally occurring composition is soy milk or STI. Additional sources of serine protease inhibitors include, for example, the following plant families: Solanaceae (e.g., potato, tomato, tomatilla, and the like); Gramineae (e.g., rice, buckwheat, sorghum, wheat, barley, oats and the like); Cucurbitaceae (e.g., cucumbers, squash, gourd, luffa and the like); and, preferably, Leguminosae (e.g., beans, peas, lentils, peanuts, and the like).

As an example, formulations can contain soybean milk or other liquid formulations derived directly from legumes or other suitable plant. In one example, such a formulation contains a large proportion of soybean milk, an emulsifier that maintains the physical stability of the soybean milk, and optionally, a chelating agent, preservatives, emollients, humectants and/or thickeners or gelling agents.

The agent in the instant compositions that specifically increases or decreases phagocytosis or ICAM-1 expression can be any type of compound known in the art. Examples include, without limitation, organic molecules, inorganic molecules, peptides, proteins, carbohydrates, nucleic acid molecules, lipids, and any combination thereof. Serine proteases and PAR-2 agonists, for example, can be used to increase phagocytosis. Trypsin, tryptase and thrombin inhibitors and PAR-2 antagonists can be used to decrease phagocytosis.

In the preferred embodiment for increasing phagocytosis, the agent is SLIGRL, SAIGRL, or SLIGKVD. In the preferred embodiment for decreasing phagocytosis, the agent is a soybean derivative (such as soybean milk, soybean paste or STI) or Compound I. Compound I has the chemical formula (SYN-Methyl-D-phenylalanyl-N-[4-[(aminoiminomethyl)amino]-1-(2-benzothiazolylcarbonyl)butyl]L-prolinamide.

This compound is described in U.S. Pat. No. 5,523,308, as well as in Costanzo, et al., J. Med. Chem., 1996, 39:3039–3043. U.S. Pat. No. 5,523,308 describes related compounds that behave as serine protease inhibitors (such as compounds with a d-phenylalanine-proline-arginine motif), and that can therefore be used to decrease phagocytosis and ICAM-1 expression.

Disorders that can be treated or prevented using the instant invention include any disorder that can be ameliorated (i.e., a positive effect on the disorder per se, and/or its secondary effects) by either an increase or decrease in phagocytosis or ICAM-1 expression in appropriate cells. In the preferred embodiment, the phagocytosis is PAR-2-mediated. These disorders include, without limitation, immune system disorders, diabetes, inflammatory disorders, disorders of the central nervous system, skin disorders, physical wounds, periodontal disorders and respiratory disorders. These disorders also include, for example, unwanted fertilization, which in one embodiment are prevented by administering inhibitors (i.e. PAR-2 inhibitors) of the sperm protease acrosin which initiates the PAR-2 pathway (for a discussion of acrosin, see Fox, et al., FEBS Lett 417:3, 267–9, 1997).

A number of disorders have characteristics of more than one category of disorder. Such disorders include, for example, adhesion disorders, which can be categorized as both skin disorders and immune system disorders. Accordingly, a statement herein that a disorder is of a particular category (e.g., skin disorder) means that, at the very least, the disorder bears traits of that category. Again, however, the disorder may additionally bear traits of another category.

Increasing the ability of immune cells to ingest foreign objects like bacteria and viruses would be expected to enhance the immune response. For example, mononuclear phagocytes are inactive in chronic microbial infections (Reiner, Immunol Today 15:8, 374–81, 1994), and their re-activation would be expected to treat the disease. Alternatively, disorders wherein the immune system is too active would be ameliorated by inhibiting phagocytosis.

Immune system and inflammatory disorders treatable in this invention include, by way of example, AIDS, chemotherapy-induced immunodeficiency, asthma, damage due to toxic substance exposure (e.g., asbestos or smoke), host rejection of implants and transplanted tissue, adhesion disorders, mild infections (such as common colds), severe infections (such as meningitis or "killer bacteria"), wounds (such as infected, diabetic, acute and chronic wounds), restenosis, cystic fibrosis, pulmonary emphysema, periodontal disease, and diaper rash.

Skin disorders include unwanted pigmentation, unwanted depigmentation, psoriasis, rashes, and certain physical skin imperfections (e.g., wrinkles). In one specific example, vitiligo patients are treated with melanin (via liposomes or plain) together with a phagocytosis-increasing agent (e.g., SLIGRL) to darken the light spots. Alternatively, they are treated with Compound I to lighten the darker sites (see U.S. Ser. No. 09/110,409, filed Jul. 6, 1998). In an example related to skin disorders, gray hair is treated with melanin (plain or liposome-delivered) and phagocytosis-increasing agent (e.g., SLIGRL), ideally in a shampoo or cream. Central nervous system disorders include, without limitation, Alzheimer's disease and other senile plaque disorders (treated via up-regulating the phagocytosis of amyloid fibrils), depression, phobic disorders, and other disorders resulting from secondary effects of benzodiazepine treatment.

The mammalian cells treated in the instant methods are preferably PAR-2-expressing cells, and include, without limitation, keratinocytes, fibroblasts, and "professional phagocytes" (i.e., cells having phagocytosis as a primary function). Professional phagocytes include, for example, neutrophils, macrophages and macrophage-like cells (e.g., Langerhans cells and Kupfer cells). In the preferred embodiment, the mammalian cells are human cells.

In this invention, the "appropriate cells" in which phagocytosis or ICAM-1 expression must be altered in response to the instant compositions of matter are readily determined based on the nature of the disorder being treated or prevented. For example, if the disorder being treated is a pigmentation disorder, the appropriate cells in which phagocytosis or ICAM-1 expression needs to be altered are keratinocytes.

The instant methods are directed at preventing as well as treating disorders. As used herein, "treating" a disorder means reducing the disorder's progression, ceasing the disorder's progression, ceasing or otherwise ameliorating secondary effects of the disorder, reversing the disorder's progression, or preferably, curing the disorder. As used herein, "preventing" a disorder means reducing, and preferably eliminating, the likelihood of the disorders occurrence.

In this invention, administering the instant compositions can be effected or performed using any of the various methods and delivery systems known to those skilled in the art. The administering can be performed, for example, intravenously, orally, via implant, transmucosally, topically, transdermally, intramuscularly, subcutaneously, and via aerosol. In addition, the instant compositions ideally contain one or more routinely used pharmaceutically or cosmetically acceptable carriers. Such carriers are well known to those skilled in the art. The following delivery systems, Which employ a number of routinely used carriers, are only representative of the many embodiments envisioned for administering the instant composition.

In one example, the instant composition is applied to the skin surface such that, based upon a square cm of skin surface, from about 2 $\mu l/cm^2$ to about 200 $\mu l/cm^2$ of phagocytosis-altering agent is present when a change in phagocytosis is desired. When using a thrombin and trypsin inhibitor such as Compound I or its analogs, whether synthetically- or naturally-derived in a formulation, such an active compound is present in an amount of from about 0.0001% to about 15% by weight/volume of the composition. In another embodiment, it is present in an amount of from about 0.0005% to about 5% of the composition. Preferably, it is present in an amount of from about 0.001 to about 1% of the composition.

Inflammatory Cell Serine Protease Inhibitors

It has also been discovered that the compounds of formula (I) are inflammatory cell serine protease inhibitors useful for the prevention and/or treatment of a variety of inflammatory-cell disorders, in particular, immunomediated inflammatory-cell disorders. As stated, the term inflammatory cell serine protease inhibitors includes, but is not limited, to leuokocytes such as mast cells, basophils, neutrophils, eosinophils, monocytes, lymphocytes and macrophages. More particularly, the compounds of formula (I) are inhibitors of mast cell serine proteases, such as tryptase and chymase, and are therefore effective for the prevention and treatment of inflammatory diseases, especially those associated with the respiratory tract, such as asthma and allergic rhinitis. In particular, the compounds, compositions and methods of the present invention are especially useful for preventing or treating the late phase bronchoconstriction and airway hyperresponsiveness associated with chronic asthma. In addition, the compounds of formula (I) may be used to prevent and/or treat other immunomediated inflammatory disorders, such as rheumatoid arthritis, rheumatoid spondylitis, osteoarthritis, gouty arthritis, arthritic conditions in general, peptic ulcers, ocular and vernal conjunctivitis, inflammatory bowel disease, Crohn's disease, urticaria, bullous pemphigoid, schleroderma, fibrosis, dermatitis, psoriasis, angioedema, eczematous dermatitis, analphylaxis, hyper proliferative skin disease, inflammatory skin conditions, hepatic cirrhosis, glomerulonephritis, nephritis, vascular inflammation, atherosclerosis, or restenosis or syncytial viral infections. The compositions for treating inflammatory cell mediated inflammatory disorders include oral, inhalant, intranasal, intravenous, suppository, and topical preparations as well as devices used to administer such preparations.

The compounds of formula (I) are prepared according to the procedures set forth in detail in U.S. Pat. No. 5,523,308. Preferred tryptase inhibitors of formula (I) for use in the methods of treating and/or preventing inflammatory disorders of the present invention include the following compounds exemplified in U.S. Pat. No. 5.523,308:

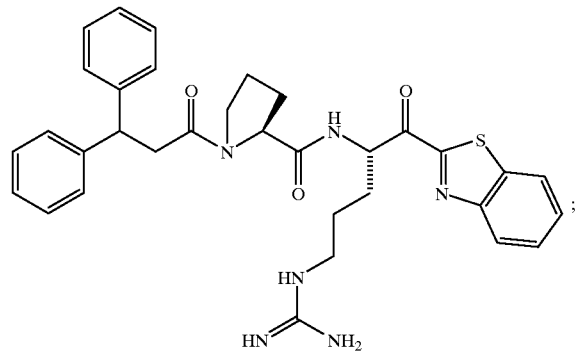

Compound 3

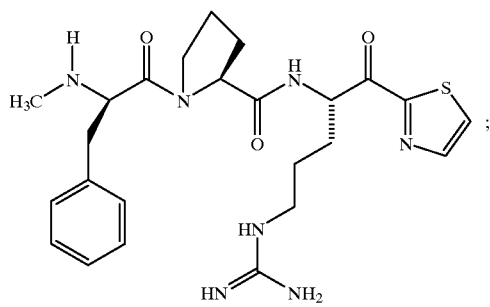

Compound 4

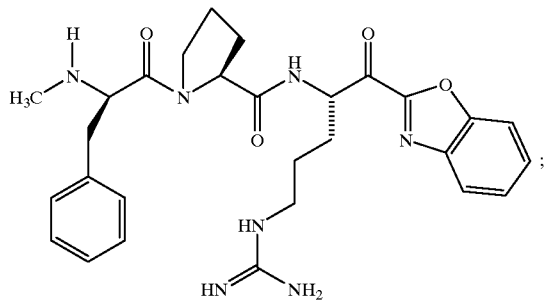

Compound 5

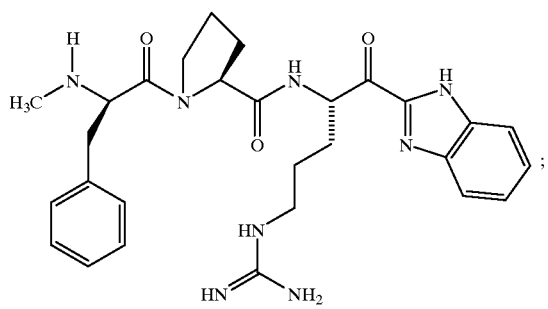

Compound 35

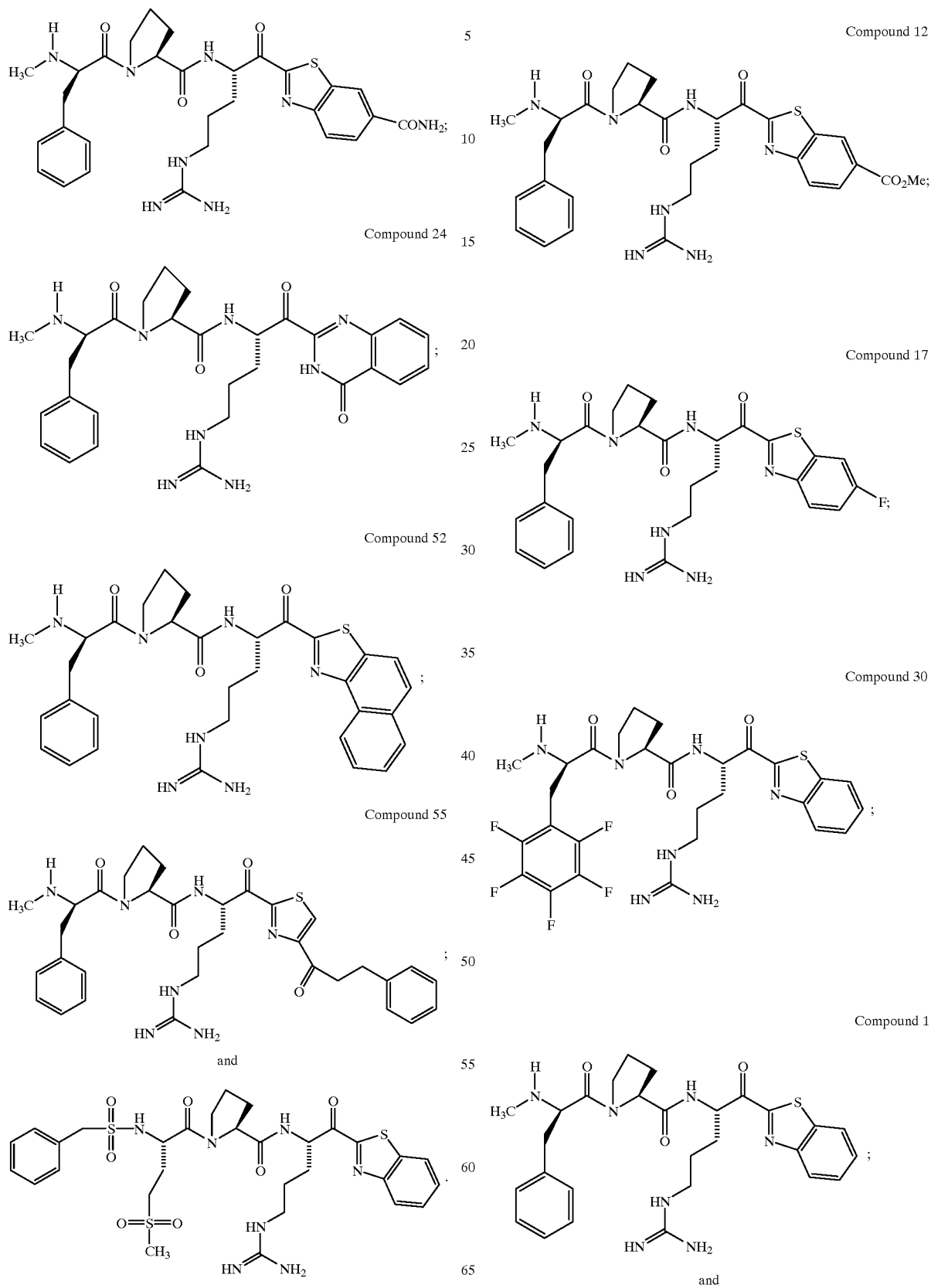
Particularly preferred tryptase inhibitor compounds of Formula I include:

Compound 31

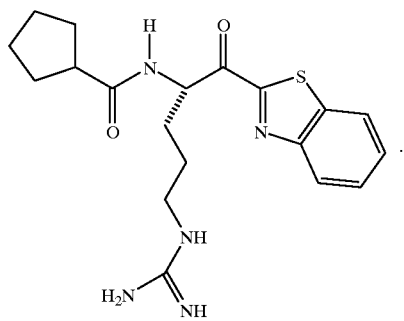

The claimed compounds are also useful as chymase inhibitors; the preferred chymase inhibitor compounds of Formula I include:

Compound 38

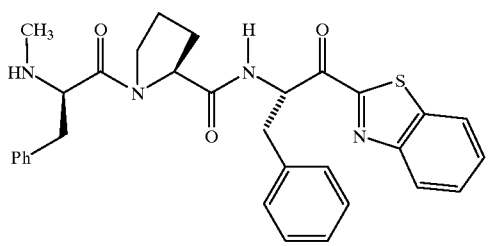

Compound 39

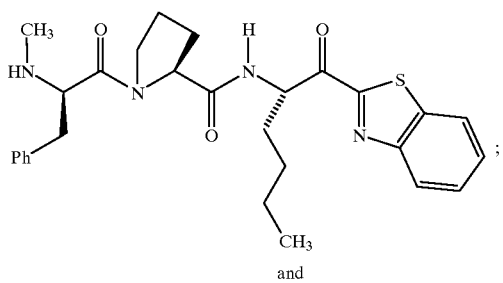

and

Compound 53

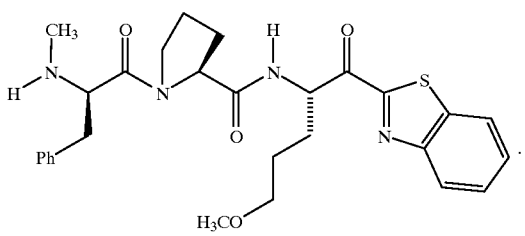

In the compounds of formula (I):

The particularly preferred "A"s are: $C_{4-8}$cycloalkylcarbonyl, 1 naphthylsulfonyl, 2-naphthylsulfonyl, substituted naphthylsulfonyls (where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy and $C_{1-4}$alkoxycarbonyl);

an L amino acid such as glycine or proline, where the amino terminus is unsubstituted or monosubstituted with a member of the group consisting of 1-naphthylsulfonyl, 2-naphthylsulfonyl and substituted naphthylsulfonyls (where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy and $C_{1-4}$alkoxycarbonyl), formyl, and phenylcarbonyl; or a poly peptide comprised of two amino acids, where the first acid is L- proline or L-pipecolinic and the second acid is D-phenylalanine, D-cyclohexylalanine, D-diphenylalanine or (2,3,4,5,6-pentafluorophenyl)alanine where the amino terminus of said second amino acid is unsubstituted or monosubstituted with a member of the group consisting of $C_{1-5}$alkyl perfluoro$C_{1-4}$alkyl or formyl.

The particularly preferred "$R_1$"s are hydrogen and methyl.

The particularly preferred "$R_2$"s are selected from the group consisting of amino$C_{2-5}$alkyl, guanidino$C_{2-5}$alkyl, amidino$C_{2-5}$alkyl, $C_{1-5}$alkylamino$C_{2-5}$alkyl, $C_{1-5}$dialkylamino$C_{2-5}$alkyl, 4-aminocyclohexyl$C_{0-2}$alkyl, 3-aminocyclohexyl$C_{0-2}$alkyl, $C_{1-4}$alkoxycarbonyl and $C_{1-5}$alkyl.

The particularly preferred "E"s are heterocycles selected from the group consisting of thiazol-2-yl, thiazol-5yl, thiazol4-yl, thiazolin-2-yl, benzoxazol-2-yl, benzimidazol-2-yl, imidazol-2-yl, 4-oxo-2-quinoxalin-2-yl, benzothiazol-2-yl, triazol-4-yl, triazol-6-yl, tetrazol-2-yl, pyrimidin-2-yl, quinolin-2-yl, pyrazol-2-yl, [4,5,6,7]-tetrahydrobenzothiazol-2-yl, naphtho[2,1 -d]thiazol-2-yl, naphtho[1,2-d]thiazol-2-yl, quinazolin-2-yl, isothiazol-5-yl, isothiazol-3-yl, purin-8-yl and a substituted heterocycle where the substituents are selected selected from $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy, $C_{1-4}$alkoxycarbonyl and hydroxy.

Moreover, in a preferred embodiment, "p" is zero so that the "B" substituent is absent and the "E" substituent is directly attached to the carbonyl group.

Biological Methods

The compounds of this invention were tested for their ability to inhibit tryptase and chymase mediated hydrolysis via an in vitro enzyme assay.

Tryptase $IC_{50}$ Method: The rate of increase in absorbance at 405 nM due to hydrolysis of synthetic chromogenic peptide substrates ([S]: 500 μM N-p-Tosyl-GLY-PRO-LYS-pNA; Sigma T-6140) is measured in the presence and absence of inhibitor compounds of formula (I) with a microplate reader at 37° C. The enzyme reaction is started by the addition of enzyme ([E]: 1.0 nM human Lung Tryptase; Cortex Biochem CP3033). Data is collected over a period of 30 min. and the initial rate of substrate hydrolysis (Vo (mOD/min)) is calculated. Inhibition is calculated by comparing to wells containing no inhibitor (vehicle) and $IC_{50}$s are determined using a four parameter fit logistics model. Chymase $IC_{50}$ Method: The rate of increase in absorbance at 405 nM due to hydrolysis of synthetic chromogenic peptide substrates ([S]: 500 μM Suc-Ala-Ala-Pro-Phe-pNA; Bachem L-1400) is measured in the presence and absence of inhibitor compounds of formula (I) with a microplate reader at 37° C. The enzyme reaction is started by the addition of enzyme ([E]: 10.0 nM Human Skin Chymase; Cortex Biochem CPl 129). Data is collected over a period of 30 min. and the initial rate of substrate hydrolysis (Vo (mOD/min)) is calculated. Inhibition is calculated by comparing to wells containing no inhibitor (vehicle) and IC$_{50}$s are determined using a four parameter fit logistics model. Chymase 10 μM Screen Method: The optical density at 405 nM due to hydrolysis of synthetic chromogenic peptide substrates ([S]: 500 μM Suc-Ala-Ala-Pro-Phe-pNA; Bachem L-1400) is measured in the presence and absence of inhibitor compounds of formula (I) with a microplate reader at room temperature. The enzyme reaction is started by the addition of enzyme ([E]: 5.0 nM Human Skin Chymase; Cortex Biochem CP1129), and 3 hours following that addition data is collected. After subtracting background (no enzyme addition), inhibition is calculated by comparing to wells containing no inhibitor (vehicle).

Since the compounds of the formula (1) are also potent thrombin inhibitors (see U.S. Pat. No. 5,523,308), an ex vivo thrombin assay was conducted to determine the duration of action of the compounds of Formula I. For this i.v. assay male rats (Long Evans, 350–500 g) were implanted with a teflon cannulae via the femoral artery while under anesthesia (pentobarbital i.p., 35 mg/kg). After surgery, the animals were individually housed in standard cages, fed with rat chow (Hanlan, #8604) and continuously infused with physiological saline to maintain arterial patency, (0.5 mL/h, intra arterial) using a spring-shielded swiveling tether connected to an infusion system. The animals were allowed to recover for at least 24 h after the surgical procedure.

A sample of blood was drawn from the animals 15 min before dosing with the inhibitor (0.25 mL blood is drawn into a syringe containing 0.025 mL of Sigma sodium citrate). The test compound was dispersed in water and delivered to the animal (0.25 mL) via the femoral vein. The inhibitor was given at a concentration (mg/mL) which produced 80% inhibition of V$_O$ in a plasma sample at 5 min after infusion. Blood was drawn from the arterial line (blood:sodium citrate, 0.25/0.025 mL) at regular intervals after dosing (5, 10, 15, 30, 60 and 120 min) and placed in a centrifuge tube. A plasma sample was obtained by centrifuging the blood at 10,000 rpm for 5 min. This sample is analyzed for thrombin inhibition using the chromogenic assay, described below.

The rate of increase in absorbance at 405 nm of synthetic peptides (50 μM Spectozyme® TH (H-D-HHT-Ala-Arg-pNA-2AcOH), American Diagnostica) is measured in the presence of plasma with a microplate reader (Molecular Devices) at 37° C. using an aqueous buffer (10 mM Tris, 10 mM Hepes, 150 mM NaCl, 0.1% PEG; pH 7.4). The buffer was added to the plasma samples (1:1) dilution prior to delivery to the microplate (1:5 and 1:50 for final plasma dilutions of 1:10 and 1:100 respectively) followed by the enzyme (1 nM human α thrombin). Datum was collected over a 30 min period and the initial rate of substrate hydrolysis (V$_0$ (mOD/min)) was calculated with an analysis program (Softmax, Molecular Devices).

The time to half plasma elimination (t ½) was calculated from the slope of V$_O$ vs. time, using the following equation: t ½=−1.6 slope. These datum are presented in Table L. In Table L, the compound # corresponds to the compound number described in U.S. Pat. No. 5,523,308.

Bioavailability was determined by an ex vivo thrombin inhibition assay which incorporated hydrolysis rates from drug administered both i.v. and p.o. In this assay male rats were prepared as described above with a Teflon tube implanted in their femoral artery. Blood was drawn from the animals 15 min before dosing with the inhibitor (0.25 mL blood was drawn into a syringe containing 0.025 mL of Sigma sodium citrate) and set aside for analysis. The test compound was dispersed in water (0.3–3.0 mg/mL final conc.) and delivered to the animals (0.25 mL) either i.v. or p.o.. Blood was drawn from the arterial line (blood:sodium citrate, 0.25/0.025 mL) at regular intervals after dosing (0.25, 0.5, 1.0, 2.0 and 3.0 h) and plasma was obtained by centrifuging the blood at 10,000 rpm for 5 min. This sample was analyzed for thrombin inhibition using the chromogenic assay, described below.

The rate of increase in absorbance at 405 nm of synthetic peptides (50 μM Spectozyme® TH (H-D-HHT-Ala-Arg-pNA-2AcOH), American Diagnostica) was measured in the presence of plasma with a microplate reader (Molecular Devices) at 37° C. using an aqueous buffer (10 mM Tris, 10 mM Hepes, 150 mM NaCl, 0.1% PEG; pH 7.4). The buffer was added to the plasma samples (1:1) dilution prior to delivery to the microplate (1:5 and 1:50 for final plasma dilutions of 1:10 and 1:100 respectively) followed by the enzyme (1 nM human α thrombin). Datum were collected over a 30 min period and the initial rate of substrate hydrolysis (V$_O$(mOD/min)) was calculated with an analysis program (Softmax, Molecular Devices).

A standard curve was generated by adding of drug or vehicle (100 μL) to whole blood (900 μL) followed by incubating (5 min) and centrifuging to obtain plasma. The percentage of thrombin inhibition was calculated by comparing the V$_0$ of the vehicle to that of the drug treated samples. Datum from several runs were normalized with a statistical package (SAS) to generate a standard curve.

The percentage of thrombin inhibition in the treated animals was calculated by comparing the V$_0$ prior to treatment with the V$_0$ obtained from samples collected after treatment. The percent inhibition was applied to the standard curve (generated above) using the statistical package (SAS) and the quantity of drug in the sample was extrapolated.

Bioavailability was calculated from the plots of the extrapolated drug in sample vs. time for both i.v. and p.o. administration using the following equation: %Bioavail, =(i.v. dose administered/p.o. dose administered) x (area under p.o. curve/area under curve i.v.)

TABLE L

| Compd. # | Tryptase IC$_{50}$ (μM) | Chymase % Inhibition (10 μM) | Chymase IC$_{50}$ | t ½ (min) | Bioavailability (%) |
|---|---|---|---|---|---|
| 1 | 0.0075 | 2 | — | 19 | 1.2 |
| 2 | 0.0402 | 1 | — | — | — |
| 3 | — | — | — | 6 | — |
| 4 | — | — | — | 16 | — |
| 5 | — | — | — | 18 | — |
| 6 | — | — | — | — | — |
| 7 | 3.9447 | 0 | — | — | — |
| 8 | — | — | — | — | — |
| 9 | — | — | — | — | — |
| 10 | — | 8 | — | — | — |
| 11 | 8.4696 | 0 | — | — | — |
| 12 | 0.0017 | 2 | — | 43 | — |
| 13 | 0.0311 | 5 | — | 25 | — |

TABLE L-continued

| Compd. # | Tryptase $IC_{50}$ ($\mu$M) | Chymase % Inhibition (10 $\mu$M) | Chymase $IC_{50}$ | t ½ (min) | Bioavailability (%) |
|---|---|---|---|---|---|
| 14 | — | — | — | — | — |
| 15 | — | — | — | 16 | — |
| 16 | — | — | — | — | — |
| 17 | 0.0111 | 3 | — | 8 | — |
| 18 | 0.1673 | 8 | — | — | — |
| 19 | 0.0179 | 2 | — | 14 | — |
| 20 | — | — | — | — | — |
| 21 | 2.1150 | 3 | — | 5 | — |
| 22 | — | — | — | — | — |
| 23 | 4.6088 | 2 | — | — | — |
| 24 | — | — | — | — | — |
| 25 | — | — | — | 14 | — |
| 26 | — | — | — | — | — |
| 27 | — | — | — | — | — |
| 28 | >10 | 0 | — | 15 | — |
| 29 | 0.0096 | 4 | — | 14 | — |
| 30 | 0.0027 | 6 | — | 6 | — |
| 31 | 0.8277 | 0 | — | — | — |
| 32 | 0.0171 | 2 | — | 19 | — |
| 33 | 0.0292 | 0 | — | 18 | — |
| 34 | 0.0256 | 3 | — | 26 | — |
| 35 | 0.0151 | 4 | — | 11 | — |
| 36 | 0.0145 | 16 | — | — | — |
| 37 | 0.0121 | 8 | — | 42 | — |
| 38 | — | 94 | 2.700 | — | — |
| 39 | >10 | 37 | — | — | — |
| 40 | >10 | 12 | — | — | — |
| 41 | 0.0054 | 3 | — | — | — |
| 42 | 0.0160 | 3 | — | — | — |
| 43 | 0.0119 | 8 | — | — | — |
| 44 | >10 | 0 | — | — | — |
| 45 | 1.7119 | 7 | — | — | — |
| 46 | — | — | — | — | — |
| 47 | — | — | — | — | — |
| 48 | >10 | 0 | — | — | — |
| 49 | >10 | 8 | — | — | — |
| 50 | 0.0159 | 5 | — | — | — |
| 51 | 0.0875 | 7 | — | 17 | — |
| 52 | 0.0337 | 4 | — | 8 | — |
| 53 | — | 5 | — | — | — |
| 54 | — | — | — | 15 | — |
| 55 | — | — | — | — | — |
| 56 | — | — | — | — | — |
| 57 | 1.7119 | 7 | — | — | — |
| 58 | 3.1404 | 0 | — | — | — |

In addition, one of ordinary skill in the art can readily determine the utility of the compounds of formula (l) to act as tryptase inhibitors for treating asthma by using an in vivo sheep model which is described in Abraham et al. *Amer. J. of Respir. and Crit. Care Med.* 1996, 154, 649–654; and Clark et al. *Amer. J. of Respir, and Crit. Care Med.* 1995, 152,2076–2083.

The terms used in describing the invention are commonly used and known to those skilled in the art. However, the terms that could have other meanings are defined. "Independently" means that when there are more than one substituent, the substitutents may be different. When a particular group is substituted (e.g., subsituted phenyl, substituted heterocycle) that group may have from one to five, (preferably, one to three, and most preferably, one or two) substituents which are independently selected. The term "alkyl" refers to straight, cyclic and branched-chain alkyl groups and "alkoxy" refers to 0-alkyl where alkyl is as defined supra. "CBZ" refers to benzyloxycarbonyl.

Typically the compounds of Formula I are isolated and used directly or as their pharmaceutically acceptable salts and prodrugs. Examples of such salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic. Examples of such prodrugs include, but are not limited to, carbamates, N-acylamidines, N-acylguanidines, ketals, and enolethers.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "amido" refers to —C(O)-NH$_2$. N-Alkylamido and N-dialkylamido refer to —C(O)-NH-alkyl and —C(O)-N(alkyl)$_2$, respectively. Similarly, sulfoxamido refers to SO$_2$-NH$_2$.

The compounds can be administered by any conventional route including but not limited to; oral, intravenous, intraperitoneal, intramuscular, subcutaneous, intranasal, topical, inhalation, suppository, and dermal patch, where the preferred route is inhalation. Doses can range from about 0.001 to about 2000 mg/kg/day (preferably, from about 0.001 to about 200 mg/kg/day) of inhibitor admixed with a suitable pharmaceutical carrier. Doses can be given in a bolus fashion or over a time period at about 0.001–2000 mg/kg/day ranging from several minutes to several days.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, via inhalation or via transdermal skin patches well known to those of ordinary skill in that art. To be administered in the form of a transdermal delivery system, the dosage administration will, of course, be continuous rather than intermittent throughout the dosage regimen.

Optimal dosages of the compounds of formula (l) to be administered for the treatment of or prevention of immuno-mediated inflammatory disorders may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

Therapeutic agents that may be useful for administration in combination with compounds of formula I include β-adrenergic agonists (e.g. albuterol, terbutaline, formoterol, fenoterol, prenaline and the like) methylxanthines (e.g. caffeine, theophylline, aminophylline, theobromine, and the like) and corticosteroids (e.g. beclomethasome, triamcinolone, flurisolide, dexamethasone, hydrocortisone, prednisone and the like). In general, one of ordinary skill in the art, acting in reliance upon personal knowledge and the disclosure of this application, will be able to ascertain the amounts of these respective therapeutic agents and the amount of the compound of the formula (I) which should be administered to a subject to treat a given immunomediated inflammatory disease. A "therapeutically effective amount," when referring to a combination of two or more agents, means an amount of each of the combined agents which is effective in eliciting the desired biological or medicial response. For example, the therapeutically effective amount of a composition comprising Compound 1 and albuterol would be the amount of Compound I and the amount of albuterol that, when taken together, have a combined effect which is therapeutically effective. In accordance with the methods of treatment of the present invention, the individual components of the combination can be administered separately at different times during the course of therapy or concurrently in divided or single combinatino forms. The instant invention is therefore to be understood as embracing all such regimes of simultaneous or alternating treatment and the term "administering" is to be interpreted accordingly.

Additionally, the method of treating immunomediated inflammatory disorders of the present invention may also be carried out using a pharmaceutical composition comprising any of the compounds of formula (I) and a pharmaceutically acceptable carrier. The compositions for treating inflammatory cell mediated inflammatory disorders include oral, inhalant, intranasal, intravenous, suppository, sustained release formulations, and topical preparations as well as devices used to administer such preparations. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Compositions useful for topical administration include liquid forms, gels, creams, ointments and sprays. Compositions suitable for inhalation include aerosolized solutions, emulsions, suspensions and dry powders. Compositions useful for parenteral administration include sterile solutions, emulsions and suspensions.

The pharmaceutical compositions can be prepared using conventional pharmaceutical excipients and compounding techniques. To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. Oral dosage forms may be elixers, syrups, capsules, pills, caplets, tablets and the like. Where the typical solid carrier is an inert substance such as lactose, starch, glucose, methyl cellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method of treating an inflammatory disorder in a subject in need thereof comprising administering to the patient a therapeutically effective amount of a compound of formula (I)

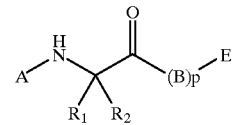

wherein:

A is selected from the group consisting of $C_{1-8}$alkyl, carboxy$C_{1-4}$alkyl, $C_{1-4}$alkoxycarbony$C_{1-4}$alkyl, phenyl$C_{1-4}$alkyl, substituted phenyl$C_{1-4}$alkyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), formyl, $C_{1-4}$alkoxycarbonyl, $C_{1-2}$alkylcarbonyl, phenyl$C_{1-4}$alkoxycarbonyl, $C_{3-7}$cycloalkylcarbonyl, phenylcarbonyl, substituted phenylcarbonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), $C_{1-4}$alkylsulfonyl, $C_{1-4}$alkoxysulfonyl, perfluoro$C_{1-4}$alkylsulfonyl, phenylsulfonyl, substituted phenylsulfonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 10-camphorsulfonyl, phenyl$C_{1-4}$alkylsulfonyl, substituted phenyl$C_{1-4}$alkylsulfonyl, $C_{1-4}$alkylsulfinyl, perfluoro$C_{1-4}$alkylsulfinyl, phenylsulfinyl, substituted phenylsulfinyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), phenyl$C_{1-4}$alkylsulfinyl, substituted phenyl$C_{1-4}$alkylsulfinyl, 1-naphthylsulfonyl, 2-naphthylsulfonyl or substituted naphthylsulfonyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, carboxy or $C_{1-4}$alkoxycarbonyl ), 1-naphthylsulfinyl, 2-naphthylsulfinyl or substituted naphthylsulfinyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl); a D or L amino acid which is coupled at its carboxy terminus to the nitrogen depicted in formula I and is selected from the group consisting of alanine, asparagine, 2-azetidinecarboxylic acid, glycine, N-$C_{1-8}$alkylglycine, proline, 1-amino-1-cyclo$C_{3-8}$alkylcarboxylic acid, thiazolidine-4-carboxylic acid, 5,5-dimethylthiazolidine-4-carboxylic acid, oxazolidine-4-carboxylic acid, pipecolinic acid, valine, methionine, cysteine, serine, threonine, norleucine, leucine, tert-leucine, isoleucine, phenylalanine, 1-naphthalanine, 2-naphthalanine, 2-thienylalanine, 3-thienylalanine, [1,2,3,4]-tetrahydroisoquinoline-1-carboxylic acid and [1,2,3,4]-tetrahydroisoquinoline-2-carboxylic acid where the amino terminus of said amino acid is connected to a member selected from the group consisting of $C_{1-4}$alkyl, tetrazol-5-yl-$C_{1-2}$alkyl, carboxy$C_{1-4}$alkyl, $C_{1-4}$alkoxycarbonyl$C_{1-4}$alkyl, phenyl$C_{1-4}$alkyl, substituted phenyl $C_{1-4}$alkyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1,1-diphenyl$C_{1-4}$alkyl, 3-phenyl-2-hydroxypropionyl, 2,2-diphenyl-1-hydroxyethylcarbonyl, [1,2,3,4]-tetrahydroisoquinoline-1-carbonyl, [1,2,3,4]-tetrahydroisoquinoline-3-carbonyl, 1-methylamino-1-cyclohexanecarbonyl, 1-hydroxy-1-cyclohexanecarbonyl, 1-hydroxy-1-phenylacetyl, 1-cyclohexyl-1-hydroxyacetyl, 3-phenyl-2-hydroxypropionyl, 3,3-diphenyl-2-hydroxypropionyl, 3-cyclohexyl-2-hydroxypropionyl, formyl, $C_{1-4}$alkoxycarbonyl, $C_{1-2}$alkylcarbonyl, perfluoro$C_{1-4}$alkyl$C_{0-4}$alkylcarbonyl, phenyl$C_{1-4}$alkylcarbonyl, substituted phenyl$C_{1-4}$alkylcarbonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl) 1,1-diphenyl$C_{1-4}$alkylcarbonyl, substituted 1,1-diphenyl$C_{1-4}$alkylcarbonyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$alkylamino, carboxy or $C_{1-4}$alkoxycarbonyl), perfluoro$C_{1-4}$alkylsulfonyl, $C_{1-4}$alkylsulfonyl, $C_{1-4}$alkoxysulfonyl, phenylsulfonyl, substituted phenylsulfonyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 10-camphorsulfonyl, phenyl$C_{1-4}$alkylsulfonyl, substituted phenyl$C_{1-4}$alkylsulfonyl, perfluoro$C_{1-4}$alkylsulfinyl, $C_{1-4}$alkylsulfinyl, phenylsulfinyl, substituted phenylsulfinyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), phenyl$C_{1-4}$alkylsulfinyl, substituted phenyl$C_{1-4}$alkylsulfinyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$-alkoxycarbonyl), 1-naphthylsulfonyl 2-naphthylsulfonyl, substituted naphthylsulfonyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{3-4}$dialkylamino, carboxy or $C_{1-4}$-alkoxycarbonyl), 1-naphthylsulfinyl, 2-naphthylsulfinyl, and substituted naphthylsulfinyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-2}$-dialkylamino, carboxy or $C_{1-4}$alkoxycarbonyl);

or a poly peptide comprised of two amino acids, where the first amino acid is a D or L amino acid, bound via its carboxy terminus to the nitrogen depicted in formula I and is selected from the group consisting of glycine, N-$C_{1-8}$alkylglycine, alanine, 2-azetidinecarboxylic acid, proline, thiazolidine-carboxylic acid, 5,5-dimethylthiazolidine-4-carboxylic acid, oxazolidine-4-carboxylic acid, 1-amino-1-cyclo$C_{3-8}$alkylcarboxylic acid, 3-hydroxyproline, 4-hydroxyproline, 3-($C_{1-4}$alkoxy)proline, 4-($C_{1-4}$alkoxy)proline, 3,4-dehydroproline, 2,2-dimethyl-4-thiazolidine carboxylic acid, 2,2-dimethyl-4-oxazolidine carboxylic acid, pipecolinic acid, valine, methionine, cysteine, asparagine, serine, threonine, leucine, tert-leucine, isoleucine, phenylalanine, 1-naphthalanine, 2-naphthalanine, 2-thienylalanine, 3-thienylalanine, [1,2,3,4]-tetrahydroisoquinoline-1-carboxylic acid, [1,2,3,4]-tetrahydroisoquinoline-2-carboxylic acid, aspartic acid-4-$C_{1-4}$alkyl ester and glutamic acid-5-$C_{1-4}$alkyl ester and the second D or L amino acid, is bound to the amino terminus of said first amino acid, and is selected from the group consisting of phenylalanine, 4-benzoylphenylalanine, 4-carboxyphenylalanine, 4-(carboxy $C_{0-2}$alkyl)phenylalanine, substituted phenylalanine (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 3-benzothienylalanine, 4-biphenylalanine, homophenylalanine, octahydroindole-2-carboxylic acid, 2-pyridylalanine, 3-pyridylalanine, 4-thiazolylalanine, 2-thienylalanine, 3-(3-benzothienyl)alanine, 3-thienylalanine, tryptophan, tyrosine, asparagine, 3-tri-$C_{1-4}$alkylsilylalanine, cyclohexylglycine, diphenylglycine, phenylglycine, methionine sulfoxide, methionine sulfone, 2,2-dicyclohexylalanine, 2-(1-naphthylalanine), 2-(2-naphthylalanine), phenyl substituted phenylalanine (where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), aspartic acid, aspartic acid-4-$C_{1-4}$alkyl ester, glutamic acid, glutamic acid-5-$C_{1-4}$alkyl ester, cyclo$C_{3-8}$alkylalanine, substituted cyclo$C_{3-8}$alkylalanine (where the ring substituents are carboxy, $C_{1-4}$alkylcarboxy, $C_{1-4}$alkoxycarbonyl or aminocarbonyl), 2,2-diphenylalanine and all alpha-$C_{1-5}$alkyl of all amino acid derivatives thereof, where the amino terminus of said second amino acid is unsubstituted or monosubstituted with a member of the group consisting of formyl, $C_{1-12}$alkyl, tetrazol-5-yl$C_{1-}$ 2alkyl, carboxyC$_{1-8}$alkyl, carboalkoxyC$_{1-4}$alkyl, phenyl C$_{1-4}$alkyl, substituted phenylC$_{1-4}$alkyl (where the phenyl substituents are independently selected from one or more of, C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl), 1,1-diphenylC$_{1-4}$alkyl, C$_{1-6}$alkoxycarbonyl, phenylC$_{1-6}$alkoxycarbonyl, C$_{1-12}$alkylcarbonyl, perfluoroC$_{1-4}$alkylC$_{0-4}$alkylcarbonyl, phenylC$_{1-4}$alkylcarbonyl, substituted phenylC$_{1-4}$alkylcarbonyl (where the phenyl substituents are independently selected from one or more of, C$_{1-4}$alkyl, perfluoro C$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl), 1,1-diphenylC$_{1-4}$alkylcarbonyl, C$_{1-4}$alkylsulfonyl, C$_{1-4}$alkoxysulfonyl, perfluoroC$_{1-4}$alkylsulfonyl, phenylsulfonyl, substituted phenylsufonyl (where the phenyl substituents are independently selected from one or more of, C$_{1-4}$alkyl, perfluoroC$_{1-4}$ alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl), 10-camphorsulfonyl, phenylC$_{1-4}$alkylsulfonyl, substituted phenylC$_{1-4}$alkylsulfonyl, C$_{1-4}$alkylsulfinyl, perfluoro C$_{1-4}$alkylsulfinyl, phenylsulfinyl, substituted phenylsufinyl (where the phenyl substituents are independently selected from one or more of, C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl), phenylC$_{1-4}$alkylsulfinyl, substituted phenylC$_{1-4}$alkylsulfinyl 1-naphthylsulfonyl, 2-naphthylsulfonyl, substituted naphthylsulfonyl (where the naphthyl substituent is selected from C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl), 1-naphthylsulfinyl, 2-naphthylsulfinyl and substituted naphthylsulfinyl (where the naphthyl substituent is selected from C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy or C$_{1-4}$alkoxycarbonyl);

R$_1$ is selected from the group consisting of hydrogen and C$_{1-5}$alkyl.

R$_2$ is selected from the group consisting of aminoC$_{2-5}$alkyl, guanidinoC$_{2-5}$alkyl, C$_{1-4}$alkylguanidinoC$_{2-5}$alkyl, diC$_{1-4}$alkylguanidinoC$_{2-5}$alkyl, amidinoC$_{2-5}$alkyl, C$_{1-4}$alkylamidinoC$_{2-5}$alkyl, diC$_{1-4}$alkylamidinoC$_{2-5}$alkyl, C$_{1-3}$alkoxy C$_{2-5}$alkyl, phenyl, substituted phenyl (where the substituents are independently selected from one or more of, amino, amidino, guanidino, C$_{1-4}$alkylamino, C$_{1-4}$dialkylamino, halogen, perfluoro C$_{1-4}$alkyl, C$_{1-4}$alkyl, C$_{1-3}$alkoxy or nitro), benzyl, phenyl substituted benzyl (where the substituents are independently selected from one or more of, amino, amidino, guanidino, C$_{1-4}$alkylamino, C$_{1-4}$dialkylamino, halogen, perfluoro C$_{1-4}$alkyl, C$_{1-4}$alkyl, C$_{1-3}$alkoxy or nitro), hydroxyC$_{2-5}$alkyl, C$_{1-5}$alkylaminoC$_{2-5}$alkyl, C$_{2-5}$dialkylaminoC$_{2-5}$alkyl, 4-aminocyclohexylC$_{0-2}$alkyl and C$_{1-5}$alkyl;

p is 0 or 1

B is

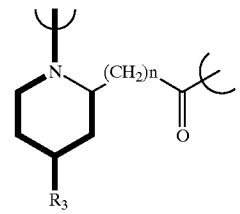

where n is 0–3, R3 is H or C$_{1-5}$alkyl and the carbonyl moiety of B is bound to E;

E is a heterocycle selected from the group consisting of oxazolin-2-yl, oxazol-2-yl, thiazol-2-yl, thiazol-5-yl, thiazol-4-yl, thiazolin-2-yl, imidazol-2-yl, 4-oxo-2-quinoxalin-2-yl, 2-pyridyl, 3-pyridyl, benzo[b] thiophen-2-yl, benzoxazol-2-yl, benzimidazol-2-yl, benzothiazol-2-yl, triazol-4-yl, triazol-6-yl, tetrazol-2-yl pyrimidin-2-yl, quinolin-2-yl, indol-2-yl, pyrazol-2-yl, 4,5,6,7-tetrahydrobenzothiazol-2-yl, naphtho[2,1-d]thiazol-2-yl, naphtho[1,2d]thiazol-2-yl quinoxalin-2-yl, isoquinolin-1-yl, isoquinolin-3-yl, benzo[b]furan-2-yl, pyrazin-2-yl, quinazolin-2-yl, isothiazol-5-yl, isothiazol-3-yl, purin-8-yl and a substituted heterocycle where the substituents are independently selected from C$_{1-4}$alkyl, perfluoro C$_{1-4}$alkyl, C$_{1-4}$alkoxy, hydroxy, halo, amido, nitro, amino, C$_{1-4}$alkylamino, C$_{1-4}$dialkylamino, carboxy, C$_{1-4}$alkoxycarbonyl, hydroxy or phenylC$_{1-4}$alkylaminocarbonyl;

and pharmaceutically acceptable salts and prodrugs thereof.

2. The method of claim 1, wherein the compound has the formula

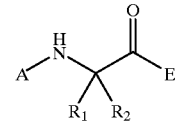

wherein

A is selected from

C$_{4-8}$cycloalkylcarbonyl, 1-naphthylsulfonyl, 2-naphthylsulfonyl, and substituted naphthylsulfonyls (where the substituents are selected from C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy and C$_{1-4}$alkoxycarbonyl);

an L amino acid such as glycine or proline, where the amino terminus is unsubstituted or monosubstituted with a member of the group consisting of 1-naphthylsulfonyl, 2-naphthylsulfonyl and substituted naphthylsulfonyls (where the substituents are selected from C$_{1-4}$alkyl, perfluoroC$_{1-4}$alkyl, C$_{1-4}$alkoxy, hydroxy, halo, amido, nitro, amino, C$_{1-4}$alkylamino, C$_{1-4}$dialkylamino, carboxy and C$_{1-4}$alkoxycarbonyl), formyl, and phenylcarbonyl; or a poly peptide comprised of two amino acids, where the first acid is L-proline or L-pipecolinic acid and the second acid is D-phenylalanine, D-cyclohexylalanine, D-diphenylalanine, methionine sulfone or (2,3,4,5,6-pentafluorophenyl)alanine where the amino terminus of said second amino acid is unsubstituted or monosubstituted with a member of the group consisting of $C_{1-5}$alkyl, perfluoro$C_{1-4}$-alkyl, phenyl$C_{1-4}$alkylsulfonyl or formyl;

$R_1$ is selected from hydrogen or methyl;

$R_2$ is selected from amino$C_{2-5}$alkyl, guanidino$C_{2-5}$alkyl, amidino$C_{2-5}$alkyl, benzyl, $C_{1-5}$alkylamino$C_{2-5}$alkyl, $C_{1-5}$dialkylamino$C_{2-5}$alkyl, 4-aminocyclohexyl$C_{0-2}$alkyl, 3-aminocyclohexyl$C_{0-2}$alkyl, $C_{1-5}$alkoxy$C_{2-5}$alkyl or $C_{1-5}$alkyl;

E is a heterocycle selected from thiazol-2-yl, thiazol-5-yl, thiazol-4-yl, thiazolin-2-yl, benzoxazol-2-yl, benzimidazol-2-yl, imidazol-2-yl, 4-oxo-2-quinoxalin-2-yl, benzothiazol-2-yl, triazol-4-yl, triazol-6-yl, tetrazol-2-yl, pyrimidin-2-yl, quinolin-2-yl, pyrazol-2-yl, [4,5,6,7]-tetrahydrobenzothiazol-2-yl, naphtho[2,1-d]thiazol-2-yl, naphtho[1,2-d]thiazol-2-yl, quinazolin-2-yl, isothiazol-5-yl, isothiazol-3-yl, purin-8-yl or a substituted heterocycle where the substituents are selected from $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy, $C_{1-4}$alkoxycarbonyl or hydroxy;

and pharmaceutically acceptable salts and prodrugs thereof.

3. The method of claim 2 wherein the compound has the formula

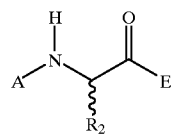

wherein

A is selected from $C_{4-8}$cycloalkylcarbonyl;

an L amino acid such as glycine or proline, where the amino terminus is unsubstituted or monosubstituted with a member of the group consisting of 1-naphthylsulfonyl, 2-naphthylsulfonyl and substituted naphthylsulfonyls (where the substituents are selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy and $C_{1-4}$alkoxycarbonyl), formyl, and phenylcarbonyl; or a poly peptide comprised of two amino acids, where the first acid is L-proline or L-pipecolinic acid and the second acid is D-phenylalanine, D-cyclohexylalanine, D-diphenylalanine, methionine sulfone or (2,3,4,5,6-pentafluorophenyl)alanine where the amino terminus of said second amino acid is unsubstituted or monosubstituted with a member of the group consisting of $C_{1-5}$alkyl, perfluoro$C_{1-4}$alkyl, phenyl$C_{1-4}$alkylsulfonyl or formyl;

E is selected from benzothiazol-2-yl or substituted benzothiazol-2-yl where the substituents are selected from $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy, $C_{1-4}$alkoxycarbonyl or hydroxy; and pharmaceutically acceptable salts and prodrugs thereof.

4. The method of claim 3, wherein the compound has the formula

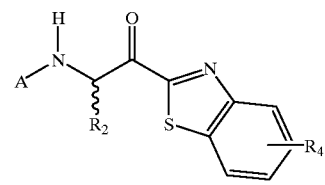

wherein $R_2$ is selected from guanidino$C_{2-5}$alkyl, benzyl, $C_{1-5}$alkoxy$C_{2-5}$alkyl or $C_{1-5}$alkyl;

$R_4$ is selected from hydrogen, halo or $C_{1-4}$alkoxycarbonyl; and pharmaceutically acceptable salts and prodrugs thereof.

5. The method of claim 4, wherein the compound is selected from

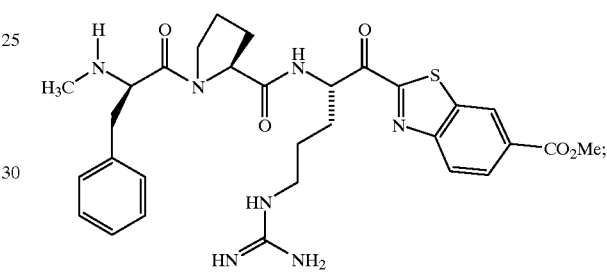

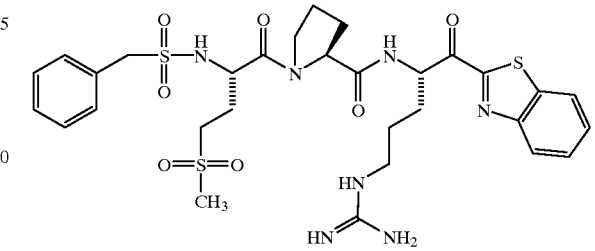

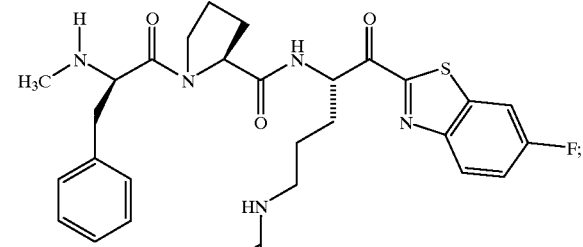

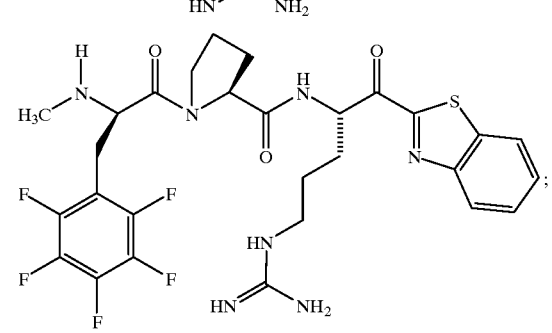

-continued

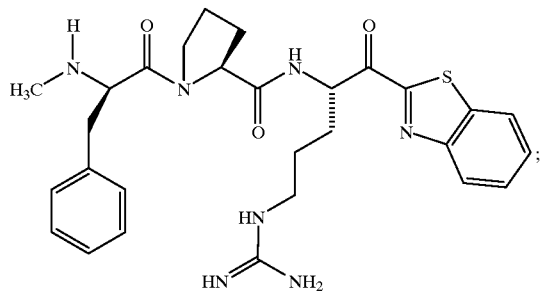

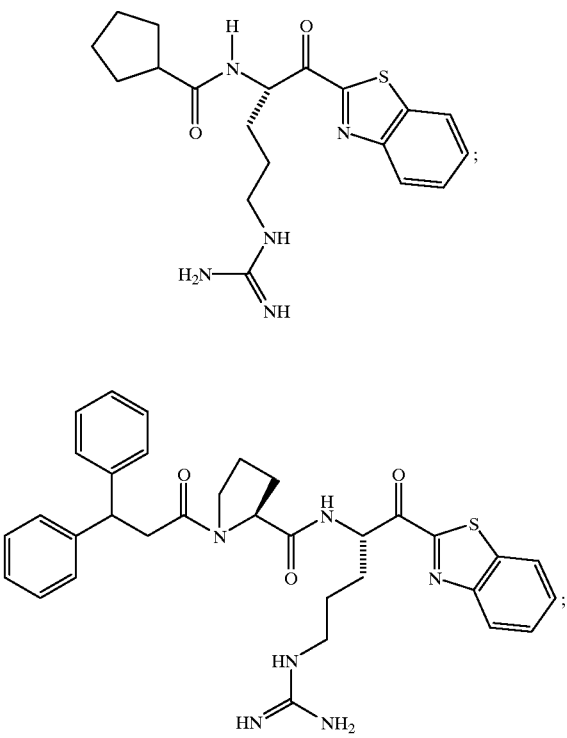

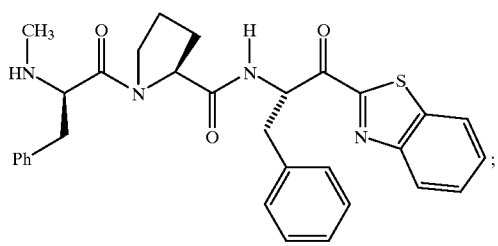

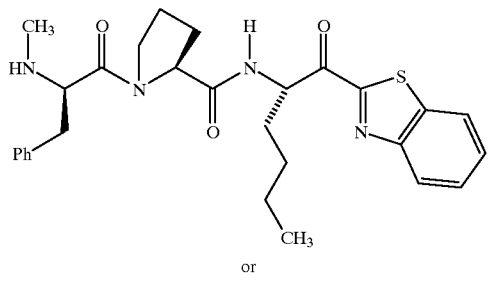

or

-continued

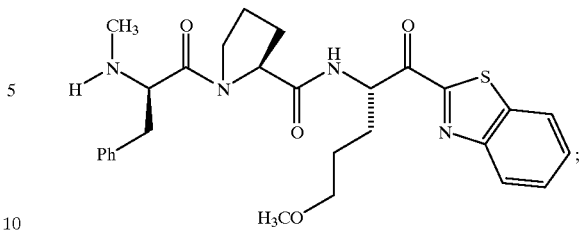

and pharmaceutically acceptable salts and prodrugs thereof.

6. The method of claim 1, wherein the inflammatory disorder is an immunomediated inflammatory disorder.

7. The method of claim 6, wherein the immunomediated inflammatory disorder is selected from asthma, allergic rhinitis, rheumatoid arthritis, rheumatoid spondylitis, osteoarthritis, gouty arthritis, arthritic conditions in general, peptic ulcers, ocular and vernal conjunctivitis, inflammatory bowel disease, Crohn's disease, urticaria, bullous pemphigoid, schleroderma, fibrosis, dermatitis, psoriasis, angioedema, eczematous dermatitis, analphylaxis, hyper proliferative skin disease, inflammatory skin conditions, hepatic cirrhosis, glomerulonephritis, nephritis, vascular inflammation, atherosclerosis, or restenosis.

8. The method of claim 6, wherein the immunomediated inflammatory disorder is a mast-cell mediated inflammatory disorder.

9. The method of claim 8, wherein the mast-cell mediated inflammatory disorder is selected from asthma or allergic rhinitis.

10. The method of claim 9, wherein the mast-cell mediated inflammatory disorder is asthma.

11. The method of claim 7, wherein the therapeutically effective amount of the compound is about 0.001 to about 2000 mg/kg/day.

12. The method of claim 11, wherein the therapeutically effective amount of the compound is about 0.001 to about 200 mg/kg/day.

13. The method of claim 5, wherein the inflammatory disorder is an immunomediated inflammatory disorder.

14. The method of claim 13, wherein the immunomediated inflammatory disorder is a mast-cell mediated inflammatory disorder.

15. The method of claim 14, wherein the mast-cell mediated inflammatory disorder is selected from asthma or allergic rhinitis.

16. The method of claim 15, wherein the mast-cell mediated inflammatory disorder is asthma.

17. The method of claim 16 wherein the compound is administered as an aerosol.

18. The method of claim 16 wherein the compound is administered in combination with a β-adrenergic agonist, a methylxanthine, a cromoglycate or a corticosteroid.

19. The method of claim 18 wherein the β-adrenergic agonist is selected from albuterol, terbutaline, formoterol, fenoterol or prenaline; the methylxanthine is selected from caffeine, theophylline, aminophylline or theobromine; the cromoglycate is selected from cromolyn or nedocromil; and the corticosteroid is selected from beclomethasome, triamcinolone, flurisolide, dexamethasone, hydrocortisone or prednisone.

20. The method of claim 1, wherein the compound is administered as a pharmaceutical composition.

21. The method of claim 20 wherein the pharmaceutical composition comprises a therapeutically effective amount of the compound of the formula I in a pharmaceutically acceptable carrier suitable for topical, oral, suppository, intranasal, inhalation or parenteral administration.

\* \* \* \* \*

UNITED STATES PATENT AND TRADEMARK OFFICE
Certificate

Patent No. 6,323,219 B1                            Patented: November 27, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael J. Costanzo, Ivyland, PA; and Miri Seiberg, Princeton, NJ.

Signed and Sealed this Third Day of August 2004.

*MARIANNE C. SEIDEL*
*Supervisory Patent Examiner*
*Art Unit 1600*